United States Patent
Liu et al.

(10) Patent No.: US 9,498,421 B2
(45) Date of Patent: *Nov. 22, 2016

(54) TWO COMPONENT COMPOSITIONS CONTAINING TETRABASIC ZINC-AMINO ACID HALIDE COMPLEXES AND CYSTEINE

(71) Applicant: Colgate-Palmolive Company, Piscataway, NJ (US)

(72) Inventors: Zhiqiang Liu, Bridgewater, NJ (US); Long Pan, Cherry Hill, NJ (US); Joseph Convery, Jackson, NJ (US); Shaotang Yuan, East Brunswick, NJ (US); Harsh M. Trivedi, Hillsborough, NJ (US)

(73) Assignee: COLGATE-PALMOLIVE COMPANY, New York, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 14/653,901

(22) PCT Filed: Nov. 7, 2013

(86) PCT No.: PCT/US2013/068860
§ 371 (c)(1),
(2) Date: Jun. 19, 2015

(87) PCT Pub. No.: WO2014/099167
PCT Pub. Date: Jun. 26, 2014

(65) Prior Publication Data
US 2016/0030319 A1 Feb. 4, 2016

Related U.S. Application Data

(63) Continuation-in-part of application No. PCT/US2013/046268, filed on Jun. 18, 2013, and a continuation-in-part of application No. PCT/US2012/070489, filed on Dec. 19, 2012, and a continuation-in-part of application No. PCT/US2012/070492, filed on Dec. 19, 2012, and a continuation-in-part of application No. PCT/US2012/070498, filed on Dec. 19, 2012, and a continuation-in-part of application No. PCT/US2012/070506, filed on Dec. 19, 2012, and a continuation-in-part of application No. PCT/US2012/070513, filed on Dec. 19, 2012, and a continuation-in-part of application No. PCT/US2012/070505, filed on Dec. 19, 2012, and a continuation-in-part of application No. PCT/US2012/070501, filed on Dec. 19, 2012, and a continuation-in-part of application No. PCT/US2012/070521, filed on Dec. 19, 2012, and a continuation-in-part of application No. PCT/US2012/070534, filed on Dec. 19, 2012, and a continuation-in-part of application No. PCT/US2012/070537, filed on Dec. 19, 2012, and a continuation-in-part of application No. PCT/US2012/070525, filed on Dec. 19, 2012, and a continuation-in-part of application No. PCT/US2013/050845, filed on Jul. 17, 2013.

(51) Int. Cl.
| | | |
|---|---|---|
| A61K 47/48 | (2006.01) | |
| A61K 33/30 | (2006.01) | |
| A61K 31/198 | (2006.01) | |
| A61K 45/06 | (2006.01) | |
| A61Q 11/00 | (2006.01) | |
| A61Q 19/00 | (2006.01) | |
| A61K 8/44 | (2006.01) | |
| A61Q 15/00 | (2006.01) | |
| A61Q 17/00 | (2006.01) | |
| A61Q 19/10 | (2006.01) | |
| A61K 8/27 | (2006.01) | |
| A61K 8/34 | (2006.01) | |

(52) U.S. Cl.
CPC ............... *A61K 8/447* (2013.01); *A61K 8/27* (2013.01); *A61K 8/345* (2013.01); *A61K 8/44* (2013.01); *A61Q 11/00* (2013.01); *A61Q 15/00* (2013.01); *A61Q 17/005* (2013.01); *A61Q 19/00* (2013.01); *A61Q 19/10* (2013.01); *A61K 2800/58* (2013.01); *A61K 2800/5922* (2013.01); *A61K 2800/882* (2013.01)

(58) Field of Classification Search
CPC .. A61K 2300/00; A61K 38/00; A61K 33/30; A61K 31/195; A61Q 11/00
See application file for complete search history.

(56) References Cited

U.S. PATENT DOCUMENTS 2,503,280 A 4/1950 Lockwood
2,507,088 A 5/1950 Bradley
(Continued)

FOREIGN PATENT DOCUMENTS

CN 101606639 12/2009
CN 102811698 12/2012
(Continued)

OTHER PUBLICATIONS

Anonymous, "Zinc Lauryl Ether Sulphate, A New Approach to Skincare,", Apr. 2004, Retrieved from Internet, http://www.erwebhosting.it/zsi/repository/Zinc%20Lauryl%20Ether%20Sulphate,%20A%20new%20approach%20to%20skin%20care.pdf, Retrieved Sep. 26, 2013.
(Continued)

*Primary Examiner* — Frederick Krass
*Assistant Examiner* — Tracy Liu

(57) ABSTRACT

Provided are compositions, e.g., oral and personal care products, comprising (i) a tetrabasic zinc-amino acid or trialkyl glycine-halide complex, and (ii) cysteine in free or in orally or cosmetically acceptable salt form, together with methods of making and using the same.

22 Claims, No Drawings

(56) References Cited

U.S. PATENT DOCUMENTS

| | | | |
|---|---|---|---|
| 2,527,686 A | 10/1950 | Sandberg | |
| 2,893,918 A | 7/1959 | Abramson | |
| 3,260,744 A | 7/1966 | Kenkichi | |
| 3,320,174 A | 5/1967 | Rubinfeld | |
| 3,372,188 A | 3/1968 | Terence | |
| 3,535,421 A | 10/1970 | Briner | |
| 3,538,730 A | 11/1970 | Morton | |
| 3,678,154 A | 7/1972 | Briner | |
| 3,741,911 A | 6/1973 | Shane | |
| 3,862,307 A | 1/1975 | Di Giulio | |
| 3,937,807 A | 2/1976 | Haefele | |
| 3,941,818 A | 3/1976 | Abdel-Monem | |
| 3,959,458 A | 5/1976 | Agricola et al. | |
| 4,051,234 A | 9/1977 | Gieske et al. | |
| 4,316,824 A | 2/1982 | Pancheri | |
| 4,339,432 A | 7/1982 | Ritchey et al. | |
| 4,340,583 A | 7/1982 | Wason | |
| 4,487,757 A | 12/1984 | Kiozpeoplou | |
| 4,565,693 A | 1/1986 | Marschner | |
| 4,599,152 A | 7/1986 | Ashmead | |
| 4,684,528 A | 8/1987 | Godfrey | |
| 4,687,663 A | 8/1987 | Schaeffer | |
| 4,842,847 A | 6/1989 | Amjad | |
| 4,866,161 A | 9/1989 | Sikes et al. | |
| 4,885,155 A | 12/1989 | Parran, Jr. et al. | |
| 5,004,597 A | 4/1991 | Majeti et al. | |
| 5,061,815 A | 10/1991 | Leu | |
| 5,156,845 A | 10/1992 | Grodberg | |
| 5,188,821 A | 2/1993 | Gaffar et al. | |
| 5,192,531 A | 3/1993 | Gaffar et al. | |
| 5,504,055 A | 4/1996 | Hsu | |
| 5,643,559 A | 7/1997 | Eigen et al. | |
| 5,698,724 A | 12/1997 | Anderson et al. | |
| 5,707,679 A | 1/1998 | Nelson | |
| 5,714,447 A | 2/1998 | Jones et al. | |
| 5,911,978 A | 6/1999 | Carr et al. | |
| 5,993,784 A | 11/1999 | Hill | |
| 6,121,315 A | 9/2000 | Nair et al. | |
| 6,156,293 A | 12/2000 | Jutila et al. | |
| 6,607,711 B2 | 8/2003 | Pedersen | |
| 6,685,920 B2 | 2/2004 | Baig et al. | |
| 6,969,510 B2 | 11/2005 | Holerca et al. | |
| 8,067,627 B2 | 11/2011 | Newsome et al. | |
| 8,247,398 B2 | 8/2012 | Goel | |
| 2004/0042978 A1 | 3/2004 | Embro | |
| 2004/0067204 A1* | 4/2004 | Wolf | A61K 8/355 424/49 |
| 2004/0122088 A1 | 6/2004 | Newsome et al. | |
| 2004/0198998 A1 | 10/2004 | Holerca et al. | |
| 2006/0024252 A1 | 2/2006 | Esposito et al. | |
| 2006/0140882 A1* | 6/2006 | Tambs | A61K 8/22 424/53 |
| 2007/0071698 A1 | 3/2007 | Doss | |
| 2007/0117741 A1* | 5/2007 | Weinberg | A61K 38/16 424/234.1 |
| 2009/0220444 A1 | 9/2009 | Teckenbrock et al. | |
| 2009/0269287 A1* | 10/2009 | Berta | A61Q 11/00 424/52 |
| 2010/0021573 A1 | 1/2010 | Gonzalez et al. | |
| 2010/0266480 A1 | 10/2010 | Huang | |
| 2010/0330163 A1* | 12/2010 | Soparkar | A23L 1/304 424/450 |
| 2011/0076309 A1 | 3/2011 | Misner et al. | |
| 2011/0229536 A1 | 9/2011 | Kvitnitsky et al. | |
| 2013/0017240 A1 | 1/2013 | Porter et al. | |
| 2014/0170086 A1 | 6/2014 | Pan et al. | |

FOREIGN PATENT DOCUMENTS

| | | |
|---|---|---|
| CN | 103156073 | 6/2013 |
| CN | 103535536 | 1/2014 |
| DE | 735096 | 5/1943 |
| EP | 0083486 | 12/1982 |
| EP | 0108937 | 5/1984 |
| EP | 0508524 | 10/1992 |
| EP | 0514553 | 11/1992 |
| EP | 0842664 | 5/1998 |
| EP | 1021158 | 7/2000 |
| EP | 1064946 | 1/2001 |
| EP | 1203575 | 5/2002 |
| EP | 1319394 | 6/2003 |
| EP | 1935395 | 6/2008 |
| EP | 1529775 | 5/2011 |
| FR | 2241301 | 3/1975 |
| GB | 2052978 | 2/1981 |
| GB | 2109685 | 6/1983 |
| GB | 2243775 | 11/1991 |
| JP | S57-158724 | 9/1982 |
| JP | 2004175790 | 6/2004 |
| JP | 2009084201 | 4/2009 |
| JP | 2010132639 | 6/2010 |
| RU | 2001104421 A | 1/2003 |
| WO | WO86/00004 | 1/1986 |
| WO | WO9917735 | 4/1999 |
| WO | WO0169087 | 9/2001 |
| WO | WO2004054531 | 7/2004 |
| WO | WO2004/064536 | 8/2004 |
| WO | WO2007063507 | 6/2007 |
| WO | WO2011053291 | 5/2011 |
| WO | WO2011/088199 | 7/2011 |
| WO | WO2011/123123 | 10/2011 |
| WO | WO2014/098813 | 6/2014 |
| WO | WO2014/098814 | 6/2014 |
| WO | WO2014/098818 | 6/2014 |
| WO | WO2014/098819 | 6/2014 |
| WO | WO2014/098821 | 6/2014 |
| WO | WO2014/098822 | 6/2014 |
| WO | WO2014/098824 | 6/2014 |
| WO | WO2014/099164 | 6/2014 |
| WO | WO2014/099165 | 6/2014 |
| WO | WO2014/099166 | 6/2014 |
| WO | WO2014/099167 | 6/2014 |
| WO | WO2014098825 | 6/2014 |
| WO | WO2014098826 | 6/2014 |
| WO | WO2014098828 | 6/2014 |
| WO | WO2014098829 | 6/2014 |
| WO | WO2014099039 | 6/2014 |
| WO | WO2014099226 | 6/2014 |
| WO | WO2014204439 | 12/2014 |

OTHER PUBLICATIONS

Deschaume et al., "Interactions of aluminum hydrolytic species with biomolecules," New Journal of Chemistry, 2008, 32:1346-1353.
European Food Safety Authority, "Scientific Opinion on the safety and efficacy of tetra-basic zinc chloride for all animal species," EFSA Journal, 2012, 10(5):2672.
Hartwell et al., "Preparation and characterization of tyrosine and lysine metal chelate polyesters and polyamides", J. of the American Chem. Society, Mar. 1970, 92(5):1284-1289.
International Search Report and Written Opinion for International Application No. PCT/US2012/074489 mailed on Oct. 22, 2013.
International Search Report and Written Opinion for International Application No. PCT/US2012/070492 mailed on Oct. 22, 2013.
International Search Report and Written Opinion for International Application No. PCT/US2012/070498 mailed on Sep. 4, 2013.
International Search Report and Written Opinion for International Application No. PCT/US2012/070501 mailed on Oct. 21, 2013.
International Search Report and Written Opinion for International Application No. PCT/US2012/070505 mailed on Nov. 20, 2013.
International Search Report and Written Opinion for International Application No. PCT/US2012/070506 mailed on Oct. 14, 2013.
International Search Report and Written Opinion for International Application No. PCT/US2012/070513 mailed on Oct. 14, 2013.
International Search Report and Written Opinion for international Application No. PCT/US2012/070521 mailed on Sep. 30, 2013.
International Search Report and Written Opinion for International Application No. PCT/US2012/070525 mailed on Sep. 27, 2013.
International Search Report and Written Opinion for International Application No. PCT/US2012/070528 mailed on Sep. 30, 2013.

(56) References Cited

OTHER PUBLICATIONS

International Search Report and Written Opinion for International Application No. PCT/US2012/070534 mailed on Sep. 26, 2013.
International Search Report and Written Opinion for International Application No. PCT/US2012/070537 mailed on Oct. 11, 2013.
International Search Report and Written Opinion for International Application No. PCT/US2013/046268 mailed on Apr. 22, 2014.
International Search Report and Written Opinion for International Application No. PCT/US2013/050845 mailed on Aug. 13, 2014.
International Search Report and Written Opinion for International Application No. PCT/US2013/068852 mailed on Nov. 10, 2014.
International Search Report and Written Opinion for International Application No. PCT/US2013/068854 mailed on Oct. 20, 2014.
International Search Report and Written Opinion for International Application No. PCT/US2013/068859 mailed on Aug. 4, 2014.
International Search Report and Written Opinion for International Application No. PCT/US2013/068860 mailed on Oct. 22, 2014.
International Search Report and Written Opinion for International Application No. PCT/US2013/070932 mailed on Jul. 24, 2014.
International Search Report and Written Opinion for International Application No. PCT/US2014/042947 mailed on Aug. 22, 2014.
International Search Report and Written Opinion for international Application No. PCT/US2014/042948 mailed on Aug. 26, 2014.
International Search Report and Written Opinion for International Application No. PCT/US2014/043051 mailed on Feb. 18, 2015.
Kondrot, "The Importance of Zinc," http://www.healingtheeye.com/Articles/zinc.html, Feb. 21, 2012.
Liang et al., "In vitro scratch assay: a convenient and inexpensive method for analysis of cell migration in vitro," Nature Protocols, 2007, 2(2):329-333.
Liu et al., "The research on zinc coordination No. 5 odd structure in zinc complex with L-lysine," J. Molecular Science, 2000, 16(2):114-117, abstract only in English.
Lu et al., "Albumin as a zinc carrier: properties of its high-affinity zincbinding site", Biochem. Soc. Trans., 2008, 36:1317-1321.
Lynch, "Zinc in the mouth, its interactions with dental enamel and possible effects on caries: a review of the literature," Int. Dent. J., Aug. 2011, Suppl 3:46-54.
Mavromichalis et al., "Growth-promoting efficacy of pharmacological doses of tetrabasic zinc chloride in diets for nursery pigs," Canadian Journal of Animal Science, pp. 387-391, Jan. 2001.
McAuliffe et al., "Metal complexes of sulphur-containing amino acids," Inorganica Chimica Acta Reviews, Dec. 1972, 6:103-121.
Moore at al., "Antibacterial activity of gutta-percha cones attributed to the tine oxide component," Oral Surgery, 1982, 53:508-517.
Mosmann, "Rapid colorimetric assay for cellular growth and survival: Application to proliferation and cytotoxicity assays," J. Immunol. Methods, 1983, 65:55-63.
Pashley et al. Dentin permeability effects of desensitizing dentifrices in vitro. J Periodontol. 1984(9):522-525.
Prasad, "Zinc:role in immunity, oxidative stress and chronic inflammation,"Current Opinion in Clinical Nutrition and Metabolic Care, 2009, 12:646-652.
Rigano, L., Zinc Lauryl Ether Sulphate—A New Approach to Skin Care, SOFW Journal, Apr. 2004, 128:26-33.
Schmetzer et al., "Wulfingite, ε-Zn(OH)2, and simonkolleite, Zn5(OH)8Cl2•H2O, two new minerals from Richelsdorf, Hesse, F.R.G.," N. Jb. Miner. Mh., Apr. 1985, pp. 145-154.
Seil et al. "Antibacterial effect of zinc oxide nanoparticles combined with ultrasound," Nanotechology,2012, 23:495101.
Soderling et al., "Betaine-containing toothpaste relieves subjective symptoms of dry mouth," Acta Odontol. Scand., Apr. 1998, 56(2):65-9.
Stewart et al., "Interdomain zinc site on human albumin," PNAS, 2003, 100(7):3701-3706.
Tian et al, "Using DGGE profiling to develop a novel culture medium suitable for oral microbial communities," Molecular Oral Microbiology, 2010, 25(5):357-367.
Twetman et al., 2003, "Caries-preveniative effect of fluoride toothpaste a systematic review," Acta Odontol Scand., Dec. 2003, 61(6):347-55.
Wachi et al., "Antibacterial compsn. Zinc oxide—solubilized by amino acid, amino acid hydrochloride and/or amino acid alkali mineral salt," Sep. 1982, vol. 1982(45).
Wallhauser et al., "Antimicrobial Preservatives in Europe: Experience with preservatives used in pharmaceuticals and cosmetics," Develop. Biol. Standard, 1974, 24:9-28.
Yao et al., "An investigation of zirconium(IV)-glycine(CP-2) hybrid complex in bovine serum albumin protein matrix under varying conditions," J. of Materials Chemistry, 2011, 21:19005-19012.
Yousef et al., "In vitro antibacterial activity and minimum inhibitory concentration of zinc oxide and nano-particle zinc oxide against pathogenic strains," J. of Health Sciences, 2012, 2(4):38-42.
Zhu et al., "Synthesis and Crystal Structure of [Zn+{H2N(CH2)4CH(NH2)COONa}2SO4~] •H20," Chinese Science Bulletin, Sep. 1990, 35(18):1521-1525.
Corresponding Office Action in RU Application No. 2015123675, mailed Aug. 31, 2016. RU.

\* cited by examiner

US 9,498,421 B2

TWO COMPONENT COMPOSITIONS CONTAINING TETRABASIC ZINC-AMINO ACID HALIDE COMPLEXES AND CYSTEINE

CROSS REFERENCE TO RELATED APPLICATIONS

This application is a United States National Stage Application under 35 U.S.C. 371 of International Application PCT/US2013/68860, filed on Nov. 7, 2013, which is a continuation in part of each of the following applications: PCT/US2013/46268, filed on 18 Jun. 2013; PCT/US2012/70489, filed on 19 Dec. 2012; PCT/US2012/70492, filed on 19 Dec. 2012; PCT/US2012/70498, filed on 19 Dec. 2012; PCT/US2012/70506, filed on 19 Dec. 2012; PCT/US2012/70513, filed on 19 Dec. 2012; PCT/US2012/70505, filed on 19 Dec. 2012; PCT/US2012/70501, filed on 19 Dec. 2012; PCT/US2012/70521, filed on 19 Dec. 2012; PCT/US2012/70534, filed on 19 Dec. 2012; PCT/US2013/70537, filed on 19 Dec. 2012; PCT/US2012/70525, filed on 19 Dec. 2012; and PCT/US2013/50845, filed on 17 Jul. 2013, all of which are incorporated herein by reference.

BACKGROUND

Conventional antiperspirants comprising salts of aluminum or aluminum/zirconium are known. These salts function as antiperspirants by forming polymeric complexes which can plug pores, thereby blocking sweat release. There is a need for additional antiperspirant active agents that provide complexes of a size capable of plugging pores to block sweat, that provide deodorant/antibacterial efficacy, and that are less irritating to the skin than the acidic salts in conventional antiperspirants. There is also a need for alternative antibacterial and skin protective agents for use in liquid hand soaps and body washes. Finally, there is a need for agents in oral care products which can whiten and strengthen teeth, retard erosion, and inhibit bacteria and plaque.

Some tetrabasic zinc-amino acid complexes, however, do not have the most optimal precipitation kinetics. In another words, their rate of precipitation upon dilution may be too slow or too fast for typical applications. For example, for oral care typical recommended brushing times range from 1 minute to 3 minutes, but an average person brushes for a significantly shorter duration. Typical recommended rinsing times with a mouthrinse is about a minute, but an average person spends much less time.

Therefore, there exists a need for optimizing the precipitation times of tetrabasic zinc halide-amino acid complexes. In particular, there is a need for reducing or delaying the precipitation times associated with the tetrabasic zinc halide-amino acid complexes.

BRIEF SUMMARY

Provided is a dual component composition to deliver a zinc precipitate to the body which comprises (i) a first component comprising a complex of tetrabasic zinc halide ("TBZH"), e.g., tetrabasic zinc chloride ("TBZC"), and an amino acid or trialkylglycine (TAG) (respectively, "TBZH-AA", "TBZC-AA", "TBZH-TAG" and "TBZC-TAG), and optionally, glycerol and (ii) a second component comprising acidified cysteine in aqueous solution with, optionally, glycerol; the first and second components being maintained separate from each other until dispensed and combined for application to the body.

The unusual and unexpected properties of this material is that the two components, when mixed, provide a rapid (instant or intentionally delayed) precipitation that allows the delivery of a zinc-containing complex to the body, in particular skin or oral cavity, making it useful in personal care products, e.g., antiperspirant products and liquid hand and body soaps, as well as in oral care products, e.g. mouthwash or dentifrice.

In general, in order to be stable tetrabasic zinc halide-amino acid complexes require an alkaline pH. Such a pH can be a problem to the user, particularly in oral applications. The present invention solves this problem by providing a dual component composition such that when the components are mixed, the resulting pH is more acceptable to the user.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

DETAILED DESCRIPTION

The following description of the preferred embodiment(s) is merely exemplary in nature and is in no way intended to limit the invention, its application, or uses.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

Tetrabasic zinc chloride (TBZC) or zinc chloride hydroxide monohydrate is a zinc hydroxy compound with the formula $Zn_5(OH)_8Cl_2 \cdot H_2O$, also referred to as basic zinc chloride, zinc hydroxychloride, or zinc oxychloride. It is a colorless crystalline solid insoluble in water. While TBZC is substantially insoluble in water, the material is found to be soluble in water in the presence of an amino acid and provides a source of zinc ions without the usage of additional anions (i.e. HCl). While TBZC is preferred in the compositions and methods of the invention, other tetrabasic zinc halides may be used, e.g., tetrabasic zinc fluoride or tetrabasic zinc bromide.

The TBZH-AA or TBZH-TAG complex contains a halide such as chloride. In one embodiment, the TBZH-AA is formed by reacting TBZH with the free base of the amino acid, in such case the halide (e.g., chloride) contribution to the complex will be primarily from TBZH. In another embodiment, the TBZH-AA is formed by reacting TBZH and a hydrohalide salt (e.g., hydrochloride salt) of a basic amino acid to obtain a complex containing TBZH the basic amino acid and halide, in such case the halide contribution to the complex will be from the TBZH and the hydrohalide salt of the amino acid. In other embodiments, a combination of the free base and hydrohalide salt of the amino acid is used as a starting material, and in other embodiments, additional halides can be provided via addition of different halide-containing compounds such as hydrochloric acid, hydrobromide acid, and the like. The types and amounts of halide source can be manipulated to achieve a desired pH. In another embodiment, the TBZH-AA is formed by reacting TBZH and trialkylglycine, such as trimethylglycine.

In one embodiment, the TBZH-AA is a TBZC-lysine complex, e.g., formed from a mixture of TBZC and lysine and/or lysine hydrochloride. This particular zinc-lysine-chloride complex is sometimes referred to herein as "TBZC-Lys".

The tetrabasic zinc-amino acid or TAG-halide complexes, e.g. TBZC-Lys, have key features (e.g., conductivity, hydrolysis reaction and protein flocculation) which make it competitive with commercial antiperspirant salts. Like conventional aluminum or aluminum-zirconium antiperspirant salts, the TBZH-AA or TBZH-TAG forms precipitates under sweat conditions that can plug the pores and block sweat release. The mechanism is unusual. As the amount of water increases, rather than going into or remaining in solution as the solution becomes more dilute, as would typically be the case for an ionic complex, the TBZH-AA or TBZH-TAG hydrolyzes, to provide a relatively insoluble zinc-containing precipitate, e.g. zinc oxide, thereby permitting further plugging of the pores and/or controlled deposition of zinc compounds on the skin. The zinc is moreover antibacterial, and so in addition to providing a precipitate which blocks sweat release from the pores, it provides a deodorant benefit by reducing odor-causing bacteria The precipitate formed from the complexes of the invention typically consists of zinc oxide, as well as other compounds and/or complexes. Zinc oxide, one constituent in the precipitate, is soluble at acidic pH, however, and as sweat has a pH of 5-6, the sweat can reduce the levels of precipitation as compared to precipitation levels at neutral or higher pH. Moreover, the sweat can gradually dissolve the depositions, reducing the duration of action of the formulation. Also, the rate of precipitation may be too slow or too rapid. These problems can be ameliorated by co-formulating the product with cysteine. The cysteine and the zinc complex together form a precipitate upon use and dilution with sweat, which precipitate can be resistant to acid. The formulation comprising TBZH-AA or TBZH-TAG together with cysteine thus has enhanced efficacy as an antiperspirant. Moreover, the cysteine helps stabilize the TBZH-AA or TBZH-TAG in the formulation prior to administration.

As the amount of water increases, the TBZH-AA or TBZH-TAG hydrolyzes to distribute a relatively insoluble zinc-containing precipitate. The precipitate typically contains one or more of zinc oxide, zinc cysteine, zinc hydroxide, or other zinc-containing compounds. This precipitate is unique in that it will allow plugging of pores on the skin. Furthermore, this reaction is atypical since, in most cases, dilution will increase the solubility of an ionic complex. Additionally, zinc is antibacterial, so it provides a precipitate which blocks sweat release from the pores while also it providing a deodorant benefit by reducing odor-causing bacteria.

It is important to note that zinc oxide is soluble at low pH, and as sweat has a pH of 5-6, the sweat can reduce the levels of precipitation of the zinc oxide compared to precipitation levels at neutral pH. Moreover, the sweat can gradually dissolve the depositions, reducing the duration of action of the formulation. This problem can be ameliorated by co-formulating the product with cysteine. The cysteine and the TBZH-AA or TBZH-TAG together form a precipitate. Upon use and dilution with sweat, the precipitate is more resistant to acid than TBZH-AA or TBZH-TAG alone. The formulation comprising TBZH-AA or TBZH-TAG together with cysteine thus has enhanced efficacy as an antiperspirant.

Although we have found that use of cysteine with the TBZH-AA or TBZH-TAG complexes form precipitates that are more resistant to sweat, we have also discovered that use of cysteine delays, or under some conditions, even inhibits formation of the precipitate. The amount of cysteine and the pH have an effect on the degree and rate of precipitate formation.

We have found that when combining cysteine with TBZH-AA or TBZH-TAG at certain pHs, rapid precipitation is the result. The precipitation is prominent even in undiluted formulas which results in storage stability problems in oral care or personal care products. Also, rapid precipitation can result in fewer zinc ions being deposited at desired body sites. We have discovered that this rapid precipitation problem can be solved by physically separating the TBZH-AA or TBZH-TAG at a high pH from the acidified cysteine at a low pH, until use or application.

The dual component compositions of the invention form visible precipitates from less than 1 second to about 20 seconds after mixing the two components even in undiluted or low-diluted form. The presence of cysteine can delay precipitation of zinc complexes, but the delay or acceleration of precipitate formation is dependent on other factors as well. The kinetics or rate of precipitation can vary depending on factors such as pH, cysteine concentration, and amount of dilution (if any). In some embodiments instantaneous precipitation of TBZH-AA or TBZH-TAG complexes is observed upon mixing the two components. As used herein, "rapid precipitation" means forming a zinc precipitate in 3 minutes or less, "instant precipitation" or "instantaneous precipitation" means forming a zinc precipitate in 1 second or less, and "delayed precipitation" means forming a zinc precipitate between 1 second and up to 3 minutes.

In preparing the two components of the composition of the invention, typically two stock solutions are prepared, each stock solution containing, respectively TBZH-AA or TBZH-TAG and acidified cysteine. To prepare the two stock solutions, several reagents are necessary. The first component of the stock solution can be prepared by utilization of a standard synthesis procedure for making TBZH-AA or TBZH-TAG. For example, preparing a TBZH-AA or TBZH-TAG stock solution includes reacting tetrabasic zinc halide, e.g., tetrabasic zinc chloride, with an amino acid hydrohalide salt, e.g., lysine-HCl, over water. Then, excess insoluble zinc material is filtered off to ultimately make a clear solution. This solution is then the stock of TBZC-AA and can be the main active ingredient in component one. Glycerol can be utilized as a co-solvent in component one as well. In the second component, the acidified cysteine stock solution can be prepared by either dissolving cysteine salt in dilute aqueous mineral acid, e.g., hydrochloric acid, or cysteine hydrohalide, such as cysteine-HCl, can be dissolved in water. Glycerol can also be utilized as a co-solvent in component two.

A two-component delivery system has been discovered to allow control of zinc complex precipitation times. The first component comprises TBZH-AA, e.g., TBZC-lys. The pH of the first component is alkaline, for example, about 7 to 11, or about 8 to about 10 or about 9 to about 10.5 or about 9 to 10. The pH of the second component is acidic, for example, about 2 to about 6 or about 2 to about 5 or about 3 to about 6 or about 4 to about 5 or about 4.5 to about 5. The pH of the second component is typically achieved by dissolving the cysteine in an acid, e.g., a mineral acid such as a hydrohalide, e.g., hydrochloric acid, and/or acidification can be achieved by dissolving cysteine monohydrohalide, e.g., monohydrochloride, in water, preferably deionized water.

It has been discovered that rapid precipitation of zinc complexes occurs at certain pHs, even without dilution. Thus, the pH of the two components when mixed is about 4 to about 8, in another embodiment about 5 to 8, in another embodiment about 5 to about 7, in another embodiment about 5.5 to about 7, and in another embodiment about 5.5 to about 6.5. The pH of each component is tailored to achieve the desired pH upon mixing to result the desired rapid rate of precipitation.

The first and second components are aqueous compositions. Typically the first component will contain about 10 to about 85% water, in another embodiment about 20 to about 85% water, in another embodiment about 20 to about 25% water, and in yet another embodiment about 30 to about 33% water. The second component will typically contain about 10% to about 95% water, in another embodiment about 20 to about 30% water, in another embodiment about 90% to about 95% water. The amount of water in each component will vary depending upon the final product form in order to achieve the desired concentration when the components are mixed. For example, dentifrices typically contain 10 to 25% total water, mouthwashes typically contain 50 to 90% total water, personal care products such as antiperspirants typically contain 10 to 20% total water. The precipitation time and pH values of the mixtures are affected by many factors, including e.g., water concentration. More water generally leads to more rapid precipitation and higher pH values of the mixture.

Provided is a dual component composition to deliver zinc to the body which comprises (i) a first component comprising a zinc tetrabasic zinc-amino acid or TAG-halide complex (TBZH-AA or TBZH-TAG) e.g., TBZC-lys, and (ii) a second component comprising cysteine in free or in orally or cosmetically acceptable salt form, the first and second components being maintained separate from each other until dispensed and combined for application to the body. The term "body" includes any site on the body where it is desirable to deposit zinc ions, e.g., skin, in particular pores of sweat glands, and the oral cavity, in particular soft and hard (teeth) tissues. The compositions may be oral care products, e.g., dentifrice or mouthrinse, or personal care products, such as antiperspirants, liquid hand soap or body wash, and skin lotions, creams and conditioners.

Upon application of the composition of the invention the first component, or component one, containing TBZH-AA or TBZH-TAG is mixed with the second component, or component two, containing acidified cysteine. The weight ratio of component one:component two after mixing is typically about 1:1, but can vary somewhat depending on the compositions of the specific components and the specific dispensing means used, for example, about 5:1 to about 1:5, in another embodiment about 1:2 to about 2:1.

The dual component TBZH-AA or TBZH-TAG/cysteine combination is useful in oral care products, for example dentifrice or mouthrinse. A dual component formulation comprising the TBZH-AA or TBZH-TAG/cysteine combination provides an effective concentration of zinc ions to the enamel, thereby protecting against erosion, reducing bacterial colonization and biofilm development, and providing enhanced shine to the teeth. Moreover, upon mixing and use, the formulation is diluted and provides a stabilized precipitate that plugs the dentinal tubules, thereby reducing the sensitivity of the teeth. While providing efficient delivery of zinc in comparison to formulations with insoluble zinc salts, the formulations comprising the TBZH-AA or TBZH-TAG/cysteine combination do not exhibit the poor taste and mouthfeel, poor fluoride delivery, and poor foaming and cleaning associated with conventional zinc-based oral care products using soluble zinc salts.

Further provided are methods of using such compositions, e.g., methods of reducing sweat comprising applying the composition to skin, methods of killing bacteria comprising contacting the bacteria with the composition, and methods of treating or reducing dental hypersensitivity, erosion, and plaque, comprising applying the composition to the teeth, as well as methods of making such compositions. In the methods of the invention the two components of the composition of the invention are mixed and applied to the body, e.g., skin or oral cavity. The mixing is typically performed just before or during application to the body so that upon application to the body the precipitate is formed at the desired site, e.g., at pores of sweat glands or at the openings of dentinal tubules. In one embodiment the two components are mixed during application, e.g., brushing with a dentifrice where the two components are applied to a toothbrush which are mixed during brushing. The methods of the invention takes advantage of the property of the precipitate being formed in 3 minutes or less after mixing to deliver maximal amount of zinc to the desired body sites.

In one embodiment, glycerol is added to the first component, second component or both which results in delay of precipitate formation, typically a delay of about 1 to 20 seconds, in one embodiment about 1 to 10 seconds, in another embodiment about 1 to 5 seconds, and in another embodiment about 1 to 3 seconds, as compared to a control formulation without glycerol. In addition to delaying precipitation, the glycerol can also function as a humectant.

The mixing can result in precipitation without dilution; however, dilution with water or an aqueous fluid such as saliva or sweat generally enhances precipitation. In a particular embodiment, a two component system is provided wherein a first component comprises the TBZH-AA or TBZH-TAG complex and the second component comprises cysteine. In the two-component system, two containers or chambers are provided containing the respective components. The cysteine is present in an amount effective to result in rapid precipitation (instant or delayed) when the two components are mixed together. In the delayed precipitation embodiment, just before or during use and application, the two components are mixed whereby the precipitate does not form while mixing, but does form at the desired body location upon application. The two component system is particularly advantageous to maximize the amount of precipitation at the desired site during use, e.g., at dentinal tubules, tooth surface, pores of sweat glands, and the like.

The dual component compositions of the present invention, e.g., dentifrices, body washes or mouthrinses, are packaged in a suitable dispensing container in which the components are maintained physically separated and from which the separated components may be dispensed synchronously, e.g., as a combined ribbon for application to a toothbrush. Such containers are known in the art. An example of such a container is a two compartment dispensing container, such as a pump or a tube, having collapsible sidewalls, as disclosed in U.S. Pat. Nos. 4,487,757 and 4,687,663; wherein, the tube body is formed from a collapsible plastic web such as polyethylene or polypropylene and is provided with a partition within the container body defining separate compartments in which the physically separated components are stored and from which they are dispensed through a suitable dispensing outlet. For mouthwashes or mouthrinses, the two components can be delivered by two separate chambers of a bottle into a mixing cup. Upon mixing, the mixture can be transferred to a human mouth and a rinse can be carried out. When the components are dispensed, they will mix in the mixing cup forming a slightly delayed precipitate that will react with appropriate kinetics as to ensure all precipitation forms within the mouth.

Provided is, in a first embodiment, a dual component composition (Composition 1) comprising (i) a first component comprising a tetrabasic zinc-amino acid or TAG-halide complex and (ii) a second component comprising acidified cysteine in free or in orally or cosmetically acceptable salt form, wherein the two components are maintained separate from each other until dispensed and combined for application to the body, e.g., 1.1. Composition 1 wherein the tetrabasic zinc halide is TBZC.
1.2. Composition 1 or 1.1 wherein the amino acid source is at least one of a basic amino acid, lysine, arginine, and glycine.
1.3. Any of the foregoing compositions, wherein the trialkyl glycine is a $C_1$-$C_4$ alkyl glycine or trimethyl glycine.
1.4. Any of the foregoing compositions wherein the pH of the first component is 7 to 11 or 8 to 10 or 9 to 10; and the pH of the second component is 4 to 8 or 5.5 to 7 or 5.5 to 6.5.
1.5. Any of the foregoing compositions wherein the two components are mixed and the pH of the resulting mixture is 5 to 8 or 5.5 to 7.
1.6. Any of the foregoing compositions wherein the first component contains 0 to 50% or 20 to 40% glycerol; or the second component contains 0 to 50% or 20 to 40% glycerol.
1.7. Any of compositions 1.-1.6 wherein the first component contains 0 to 50% or 20 to 40% glycerol; and the second component contains 0 to 50% or 20 to 40% glycerol.
1.8. Any of the foregoing compositions wherein the zinc amino acid halide is made by combining TBZX with an amino acid.
1.9. Any of the foregoing Compositions which upon dilution with water, provides a precipitate comprising zinc oxide in complex with cysteine, and optionally additionally comprising zinc oxide, zinc carbonate, and mixtures thereof.
1.10. Any of the foregoing compositions wherein the total amount of zinc present in the composition when the two components are mixed is about 0.2 to about 9%, or about 0.6 to about 1% or about 2% to about 3% by weight of the total composition.
1.11. Any of the foregoing composition the about of zinc present in the first component is about 0.6% to about 2%, or about 0.8% to about 1.5% or about 1% to about 1.2% by weight of the first component.
1.12. Any of the foregoing compositions wherein the ratio of zinc to cysteine is from about 5:1 to about 10:1 by weight of the total composition.
1.13. Any of the foregoing compositions, wherein the cysteine is a cysteine hydrohalide, optionally cysteine hydrochloride.
1.14. Any of the foregoing compositions wherein a zinc precipitate forms within 30 seconds, or 1 second to 30 seconds, or 1 to 15 seconds or 1 to 3 seconds after mixing the two components.
1.15. Any of the foregoing compositions further comprising an orally or cosmetically acceptable carrier in the first component, second component or both.
1.16. Any of the foregoing compositions further comprising an orally or cosmetically acceptable carrier, and which is an oral care product selected from dentifrice or mouthwash, or a personal care product, selected from antiperspirants, deodorants, liquid hand soap, body wash, dermal lotions, dermal creams, and dermal conditioners.
1.17. Any of the foregoing compositions wherein the first component contains about 10% to about 85% water, or about 20 to about 85% water, or about 20 to about 25% water, or about 30 to about 33% water, and the second component contains about 10% to about 95% water or about 20 to about 30% water, or about 40% to about 50% water.

Provided is a method of making composition 1, et seq. comprising (i) combining a zinc ion source, an amino acid or TAG source, a halide source (wherein the halide source can be part of the zinc ion source, the amino acid or TAG source, or a halogen acid), in a fluid (e.g., aqueous) medium optionally containing glycerol, optionally isolating the complex thus formed in solid form and placing the material thus formed into a first container, (ii) placing cysteine optionally with glycerol, and optionally with a hydrohalide, in a second container physically separate from the first container. Either or both of the materials in the separate containers can optionally be combined with a cosmetically or orally acceptable carrier.

Provided is a composition (Composition 2) which is an antiperspirant or deodorant product comprising (i) a first component comprising a tetrabasic zinc-amino acid or TAG-halide complex and (ii) a second component comprising acidified cysteine in free or in orally or cosmetically acceptable salt form, wherein the two components are maintained separate from each other until dispensed and combined for application to the body, and wherein either or both components additionally comprise a cosmetically acceptable carrier, e.g. in accordance with any of the scopes of Composition 1, et seq., e.g.

2.1. Composition 2 which, upon mixing and use, provides a precipitate to the skin, comprising zinc oxide in complex with cysteine, and optionally additionally comprising zinc oxide, zinc carbonate, and mixtures thereof.
2.2. Composition 2 or 2.1 wherein tetrabasic zinc halide complex is TBZC, optionally in hydrate form.
2.3. Composition 2 or 2.1 wherein the cosmetically acceptable carrier comprises one or more ingredients selected from water-soluble alcohols (such as $C_{2-8}$ alcohols including ethanol); glycols (including propylene glycol, dipropylene glycol, tripropylene glycol and mixtures thereof); glycerides (including mono-, di- and triglycerides); medium to long chain organic acids, alcohols and esters; surfactants (including emulsifying and dispersing agents); additional amino acids; structurants (including thickeners and gelling agents, for example polymers, silicates and silicon dioxide); emollients; fragrances; and colorants (including dyes and pigments).
2.4. Composition 2, 2.1, or 2.2 wherein the composition is in the form of an aerosol antiperspirant spray.

Also provided are methods of reducing perspiration comprising mixing both components and applying an antiperspirant effective amount of any of Composition 2, et seq. to the skin, methods of reducing body odor comprising mixing both components and applying a deodorant-effective amount of any of Composition 2, et seq. to the skin, and methods of killing bacteria comprising mixing both components and contacting the bacteria with any of Composition 2, et seq. For example, provided is (i) a method for controlling perspiration comprising mixing both components and applying to skin an antiperspirant effective amount of a formulation of any embodiment embraced or specifically described herein, e.g., any of Composition 2, et seq.; and (ii) a method for controlling odor from perspiration or bacteria on the skin, comprising mixing both components and applying to skin a deodorant effective amount of a formulation of any embodiment embraced or specifically described herein, e.g., any of Composition 2, et seq.

Provided is a method of making an antiperspirant or deodorant comprising (i) a first component comprising a tetrabasic zinc halide and (ii) a second component physically separate from the first component comprising cysteine in free or cosmetically acceptable salt form, e.g., any of Composition 2, et seq. comprising combining a cosmetically acceptable carrier, and optionally glycerol, with zinc amino acid halide in the first component, and/or with cysteine in the second component.

Also provided is (i) the use of any of Composition 2, et seq. to kill bacteria, reduce perspiration, and/or reduce body odor; and (iii) any of Composition 2, et seq. for use in killing bacteria, reducing perspiration, and/or reducing body odor.

Also provided is the use of cysteine in the manufacture of an antiperspirant or deodorant formulation, e.g., a formulation according to any of Composition 2, et seq.

In making Composition 2, et seq. the tetrabasic zinc-amino acid halide and cysteine in free or cosmetically acceptable salt form can be incorporated into a suitable, cosmetically acceptable base, for example a spray, aerosol, stick, or roll-on for application to the underarm wherein the first and second components mix when forming an aerosol or when contacted through a nozzle or other dispensing means. Following application, in the presence of charged molecules such as proteins found on the skin, the salt will flocculate, forming plugs which block sweat release. Additional water from sweat can moreover dilute the formulation, causing the complex to decompose, resulting in a precipitate composed primarily of zinc oxide in complex with cysteine, which can reduce sweat and odor as described above.

As used herein, the term antiperspirant can refer generally to any product that can form a plug in a pore to reduce sweating, including those materials classified as antiperspirants by the Food and Drug Administration under 21 CFR part 350. It is understood that antiperspirants may also be deodorants, particularly in the case of the described compositions, as zinc has antibacterial properties and thus inhibits odor-causing bacteria on the skin.

Also provided is a composition (Composition 3) which is a personal care product selected from liquid hand soap, body wash, dermal lotions, dermal creams, and dermal conditioners comprising (i) a first component comprising a tetrabasic zinc-amino acid or TAG-halide complex and (ii) a second component comprising acidified cysteine in free or in orally or cosmetically acceptable salt form, wherein the two components are maintained separate from each other until dispensed and combined for application to the body, and wherein either or both components additionally comprise a cosmetically acceptable carrier, e.g. in accordance with any of the scopes of Composition 1, et seq., e.g.:

3.1. Composition 3 which, upon mixture of both components and use, provides a precipitate to the skin, comprising zinc oxide in complex with cysteine, and optionally additionally comprising zinc oxide, zinc carbonate, and mixtures thereof.

3.2. Composition 3 or 3.1 comprising the tetrabasic zinc halide complex in an amount of 1 to 10% by weight of the total composition.

3.3. Any of the foregoing compositions, wherein a total amount of zinc present in the total composition is 0.1 to 8 weight %, or 0.1 to 2 or 0.1 to 1 weight %.

3.4. Any of the foregoing compositions, wherein the cysteine is a cysteine hydrohalide, optionally cysteine hydrochloride.

3.5. Any of the foregoing compositions wherein the cosmetically acceptable carrier comprises one or more ingredients selected from water-soluble alcohols (such as $C_{2-8}$ alcohols including ethanol); glycols (including propylene glycol, dipropylene glycol, tripropylene glycol and mixtures thereof); glycerides (including mono-, di- and tri-glycerides); medium to long chain organic acids, alcohols and esters; surfactants (including emulsifying and dispersing agents); additional amino acids; structurants (including thickeners and gelling agents, for example polymers, silicates and silicon dioxide); emollients; fragrances; and colorants (including dyes and pigments).

3.6. Any of the foregoing compositions, wherein the cosmetically acceptable carrier comprises one or more non-ionic surfactants, for example non-ionic surfactants selected from amine oxide surfactants (e.g., fatty acid amides of alkyl amines, for example lauramidopropyldimethylamine oxide, myristamidopropylamine oxide and mixtures thereof), alcohol amide surfactants (e.g., fatty acid amides of alcohol amines, e.g., cocamide MEA (cocomonoethanolamine)), polyethoxylated surfactants (e.g. polyethoxylated derivatives of esters of fatty acids and polyols (for example glycols, glycerols, saccharides or sugar alcohols), for example polysorbates or PEG-120 methyl glucose dioleate), and combinations thereof.

3.7. Any of the foregoing compositions wherein the cosmetically acceptable carrier comprises an anionic surfactant, e.g. selected from sodium lauryl sulfate and sodium ether lauryl sulfate.

3.8. Any of the foregoing compositions wherein the cosmetically acceptable carrier comprises water, an anionic surfactant, e.g., sodium laureth sulfate, a viscosity modifying agent, e.g., acrylates copolymer, and a zwitterionic surfactant, e.g., cocamidopropyl betaine.

3.9. Any of the foregoing compositions wherein the cosmetically acceptable carrier is substantially free of anionic surfactants.

3.10. Any of the foregoing compositions wherein the cosmetically acceptable carrier comprises water, quaternary ammonium agents (e.g. cetrimonium chloride), humectant (e.g. glycerin), and non-ionic surfactant (e.g., selected from amine oxide surfactants (e.g., lauramidopropyldimethylamine oxide myristamidopropylamine oxide and mixtures thereof), alcohol amide surfactants (e.g., cocamide MEA (cocomonoethanolamine)), polyethoxylate surfactants (e.g. PEG-120 methyl glucose dioleate), and combinations thereof).

3.11. Any of the foregoing compositions, wherein the cosmetically acceptable carrier comprises an antibacterially effective amount of a non-zinc antibacterial agent, e.g., an antibacterial agent selected from triclosan, triclocarban, chloroxylenol, herbal extracts and essential oils (e.g. rosemary extract, tea extract, magnolia extract, thymol, menthol, eucalyptol, geraniol, carvacrol, citral, hinokitol, catechol, methyl salicylate, epigallocatechin gallate, epigallocatechin, gallic acid), bisguanide antiseptics (e.g., chlorhexidine, alexidine or octenidine), and quaternary ammonium compounds (e.g., cetylpyridinium chloride (CPC), benzalkonium chloride, tetradecylpyridinium chloride (TPC), N-tetradecyl-4-ethylpyridinium chloride (TDEPC)); and combinations thereof; for example an antibacterially effective amount of benzalkonium chloride.

3.12. Any of the foregoing compositions which has pH of about 5 to about 8, or 5 to 7, when the two components are mixed.

3.13. Any of the foregoing compositions comprising ingredients as follows:

| Material | Weight % |
| --- | --- |
| Water | 80-90% |
| Quaternary ammonium antibacterial agents, e.g., selected from cetrimonium chloride (cetyl trimethyl ammonium chloride), $C_{12-13}$ alkydimethylbenzyl ammonium chloride (BKC), and combinations thereof | 0.1-4% |
| Humectants, e.g, glycerin | 1-3% |
| Non-ionic surfactant, e.g., selected from amine oxide surfactants (e.g., lauramidopropyldimethylamine oxide myristamidopropylamine oxide and mixtures thereof), alcohol amide surfactants (e.g., cocamide MEA (cocomonoethanolamide)), polyethoxylate surfactants (e.g. PEG-120 methyl glucose dioleate), and combinations thereof | 1-5% |
| Buffering agents and agents to adjust pH | 1-3% |
| Preservatives and/or chelators | 0.1-2% |
| Fragrance and coloring agents | 0.1-2% |
| TBZC-lys | 1-5%, e.g., 3-4% |
| Cysteine | 0.1-1%, e.g. 0.5% | wherein the formulation is in a container that has a divided chamber; one chamber containing the above base with cysteine and the other containing the above base with TBZC-lys.

Also provided are methods of killing bacteria comprising mixing both components and contacting the bacteria with an antibacterially effective amount of the mixture, e.g., with any of Composition 3, et seq., for example, methods of treating or reducing the incidence of topical skin infections, for example infections by *Staphylococcus aureus* and/or *Streptococcus pyogenes*, as well as to treat or reduce the incidence of acne, comprising washing the skin with an antibacterially effective amount of a TBZH-AA or TBZH-TAG and cysteine, e.g., with any of Composition 3, et seq., and water.

Also provided is a method of making a personal care comprising (i) a first component comprising a tetrabasic zinc-amino acid halide and (ii) a second component physically separate from the first component comprising cysteine in free or cosmetically acceptable salt form, e.g., any of Composition 3, et seq. comprising combining a cosmetically acceptable carrier, and optionally glycerol, with tetra basic zinc amino acid halide in the first component, and/or with cysteine in the second component.

Also provided is (i) the use of a dual component composition containing TBZH-AA or TBZH-TAG complex and cysteine, e.g., any of Compositions 1, et seq., to kill bacteria, to protect the skin, e.g., from bacteria or to provide a visual signal when washing; (ii) the use of a TBZH-AA or TBZH-TAG and cysteine in the manufacture of a composition, any of Compositions 1, et seq., to kill bacteria, to protect the skin, or to provide a visual signal when washing; and (iii) TBZH-AA or TBZH-TAG and cysteine, e.g., any of Compositions 1, et seq., for use to kill bacteria, to protect the skin, or to provide a visual signal when washing.

For example, in one embodiment, either the first component comprising the tetrabasic zinc halide-amino acid complex or the second component comprising the cysteine, or both are mixed with conventional commercial liquid hand soap formulation ingredients comprising surfactants and optionally benzalkonium chloride. Upon mixing both components and dilution a white precipitate is instantaneously formed. Thus, the composition of the invention can provide a visual/sensory trigger for the washing process. The precipitate, composed of ZnO stabilized by cysteine, is deposited on skin and thus enhances the antimicrobial effect of the LHS.

Also provided is a composition (Composition 4) which is an oral care product, e.g., a dentifrice or mouthrinse, comprising (i) a first component comprising a tetrabasic zinc-amino acid or TAG-halide complex and (ii) a second component comprising acidified cysteine in free or in orally or cosmetically acceptable salt form, wherein the two components are maintained separate from each other until dispensed and combined for application to the oral cavity, and wherein either or both components additionally comprise an orally acceptable carrier, e.g. in accordance with any of the scopes of Composition 1, et seq., e.g.:

4.1. Composition 4 in the form of a dentifrice which upon mixing and application to the teeth provides a precipitate to the teeth, comprising zinc oxide in complex with cysteine, and optionally additionally comprising zinc oxide, zinc carbonate, and mixtures thereof.

4.2. Composition 4 or 4.1 in the form of a dentifrice wherein the tetrabasic zinc-amino acid halide complex is present in an effective amount, e.g., in an amount of 0.5-4% by weight of zinc, e.g., 1-3% by weight of zinc of the total composition, and wherein the orally acceptable carrier is a dentifrice base.

4.3. Any of the foregoing compositions 4-4.3 in the form of a dentifrice, wherein the orally acceptable carrier is a dentifrice base comprising an abrasive, e.g., an effective amount of a silica abrasive, e.g., 10-30%, e.g., 20%.

4.4. Any of the foregoing compositions wherein the tetrabasic zinc amino acid halide complex is present in an effective amount, e.g., in an amount of 0.1-3% by weight of zinc, e.g., 0.2-1% by weight of zinc of the total composition.

4.5. Any of the foregoing compositions, wherein the cysteine is a cysteine hydrohalide, optionally cysteine hydrochloride.

4.6. Any of the foregoing compositions further comprising an effective amount of a fluoride ion source, e.g., providing 500 to 3000 ppm fluoride based on the total composition.

4.7. Any of the foregoing compositions further comprising an effective amount of fluoride, e.g., wherein the fluoride is a salt selected from stannous fluoride, sodium fluoride, potassium fluoride, sodium monofluorophosphate, sodium fluorosilicate, ammonium fluorosilicate, amine fluoride (e.g., N'-octadecyltrimethylendiamine-N,N,N'-tris(2-ethanol)-dihydrofluoride), ammonium fluoride, titanium fluoride, hexafluorosulfate, and combinations thereof.

4.8. Any of the preceding compositions comprising an effective amount of one or more alkali phosphate salts, e.g., sodium, potassium or calcium salts, e.g., selected from alkali dibasic phosphate and alkali pyrophosphate salts, e.g., alkali phosphate salts selected from sodium phosphate dibasic, potassium phosphate dibasic, dicalcium phosphate dihydrate, calcium pyrophosphate, tetrasodium pyrophosphate, tetrapotassium pyrophosphate, sodium tripolyphosphate, and mixtures of any of two or more of these, e.g., in an amount of 1-20%, e.g., 2-8%, e.g., ca. 5%, by weight of the composition.

4.9. Any of the foregoing compositions comprising buffering agents, e.g., sodium phosphate buffer (e.g., sodium phosphate monobasic and disodium phosphate).

4.10. Any of the foregoing compositions comprising a humectant, e.g., selected from sorbitol, propylene glycol, polyethylene glycol, xylitol, and mixtures thereof. Any of the preceding compositions comprising one or more surfactants, e.g., selected from anionic, cationic, zwitterionic, and nonionic surfactants, and mixtures thereof, e.g., comprising an anionic surfactant, e.g., a surfactant selected from sodium lauryl sulfate, sodium ether lauryl sulfate, and mixtures thereof, e.g. in an amount of from 0.3% to 4.5% by weight, e.g. 1-2% sodium lauryl sulfate (SLS); and/or a zwitterionic surfactant, for example a betaine surfactant, for example cocamidopropylbetaine, e.g. in an amount of from 0.1% to 4.5% by weight of the total composition, e.g. 0.5-2% cocamidopropylbetaine.

4.11. Any of the preceding compositions further comprising a viscosity modifying amount of one or more of polysaccharide gums, for example xanthan gum or carrageenan, silica thickener, and combinations thereof.

4.12. Any of the preceding compositions further comprising flavoring, fragrance and/or coloring.

4.13. Any of the foregoing compositions comprising an effective amount of one or more antibacterial agents, for example comprising an antibacterial agent selected from halogenated diphenyl ether (e.g. triclosan), herbal extracts and essential oils (e.g., rosemary extract, tea extract, magnolia extract, thymol, menthol, eucalyptol, geraniol, carvacrol, citral, hinokitol, catechol, methyl salicylate, epigallocatechin gallate, epigallocatechin, gallic acid, miswak extract, sea-buckthorn extract), bisguanide antiseptics (e.g., chlorhexidine, alexidine or octenidine), quaternary ammonium compounds (e.g., cetylpyridinium chloride (CPC), benzalkonium chloride, tetradecylpyridinium chloride (TPC), N-tetradecyl-4-ethylpyridinium chloride (TDEPC)), phenolic antiseptics, hexetidine, octenidine, sanguinarine, povidone iodine, delmopinol, salifluor, metal ions (e.g., zinc salts, for example, zinc citrate, stannous salts, copper salts, iron salts), sanguinarine, propolis and oxygenating agents (e.g., hydrogen peroxide, buffered sodium peroxyborate or peroxycarbonate), phthalic acid and its salts, monoperthalic acid and its salts and esters, ascorbyl stearate, oleoyl sarcosine, alkyl sulfate, dioctyl sulfosuccinate, salicylanilide, domiphen bromide, delmopinol, octapinol and other piperidino derivatives, nicin preparations, chlorite salts; and mixtures of any of the foregoing; e.g., comprising triclosan or cetylpyridinium chloride.

4.14. Any of the foregoing compositions comprising an antibacterially effective amount of triclosan, e.g. 0.1-0.5%, e.g. 0.3% by weight of the total composition.

4.15. Any of the preceding compositions further comprising a whitening agent, e.g., a selected from the group consisting of peroxides, metal chlorites, perborates, percarbonates, peroxyacids, hypochlorites, and combinations thereof.

4.16. Any of the preceding compositions further comprising hydrogen peroxide or a hydrogen peroxide source, e.g., urea peroxide or a peroxide salt or complex (e.g., such as peroxyphosphate, peroxycarbonate, perborate, peroxysilicate, or persulphate salts; for example calcium peroxyphosphate, sodium perborate, sodium carbonate peroxide, sodium peroxyphosphate, and potassium persulfate);

4.17. Any of the preceding compositions further comprising an agent that interferes with or prevents bacterial attachment, e.g., solbrol or chitosan.

4.18. Any of the preceding compositions further comprising a source of calcium and phosphate selected from (i) calcium-glass complexes, e.g., calcium sodium phosphosilicates, and (ii) calcium-protein complexes, e.g., casein phosphopeptide-amorphous calcium phosphate 4.19. Any of the preceding compositions further comprising a soluble calcium salt, e.g., selected from calcium sulfate, calcium chloride, calcium nitrate, calcium acetate, calcium lactate, and combinations thereof.

4.20. Any of the preceding compositions further comprising a physiologically or orally acceptable potassium salt, e.g., potassium nitrate or potassium chloride, in an amount effective to reduce dentinal sensitivity.

4.21. Any of the foregoing compositions further comprising an anionic polymer, e.g., a synthetic anionic polymeric polycarboxylate, e.g., wherein the anionic polymer is selected from 1:4 to 4:1 copolymers of maleic anhydride or acid with another polymerizable ethylenically unsaturated monomer; e.g., wherein the anionic polymer is a methyl vinyl ether/maleic anhydride (PVM/MA) copolymer having an average molecular weight (M.W.) of 30,000 to 1,000,000, e.g. 300,000 to 800,000, e.g., wherein the anionic polymer is 1-5%, e.g., 2%, of the weight of the total composition.

4.22. Any of the preceding compositions further comprising a breath freshener, fragrance or flavoring.

4.23. Any of the foregoing compositions, wherein the pH of the total composition after mixing is approximately 4 to 8 or 5 to 7.

4.24. Any of the foregoing compositions in the form of an oral gel, wherein the amino acid is lysine and the halide is chloride, in an amount to provide 0.1-8%, e.g., 0.5% zinc by weight, and further comprising humectant, e.g., sorbitol, propylene glycol and mixtures thereof, e.g., in an amount of 45-65%, e.g., 50-60%. thickeners, e.g., cellulose derivatives, e.g., selected from carboxymethyl cellulose (CMC), trimethyl cellulose (TMC) and mixtures thereof, e.g., in an amount of 0.1-2%, sweetener and/or flavorings, and water, e.g., an oral gel comprising

| Ingredients | % |
| --- | --- |
| Sorbitol | 40-60%, e.g., 50-55% |
| TBZC | to provide 0.1-2% Zn, e.g 0.5% Zn |
| Cysteine | 0.02-0.5%, e.g., 0.1% |

-continued

| Ingredients | % |
|---|---|
| Carboxymethyl cellulose (CMC) and Trimethyl cellulose (TMC) | 0.5-1%, e.g., 0.7% |
| Flavoring and/or sweetener | 0.01-1% |
| Propylene Glycol | 1-5%, e.g., 3.00% | wherein the formulation is in a tube that has a dual chamber system that separates one side from the other; or, the system has a high enough density difference that allows for almost complete separation of the two stocks or components.

4.25. Any of the forgoing compositions for use to reduce and inhibit acid erosion of the enamel, clean the teeth, reduce bacterially-generated biofilm and plaque, reduce gingivitis, inhibit tooth decay and formation of cavities, and reduce dentinal hypersensitivity.

The dentifrice of the invention can be placed in a dual chamber tube, each chamber containing one of the respective components. Each component can contain a dentifrice base, e.g., a gel base, as well as either cysteine or TBZH-AA or TBZH-TAG. When the tube is squeezed both reagents will come out at the same time and mixing will take place in-vitro while brushing with the aid of the dentifrice base.

Also provided are methods to reduce and inhibit acid erosion of the enamel, clean the teeth, reduce bacterially-generated biofilm and plaque, reduce gingivitis, inhibit tooth decay and formation of cavities, and reduce dentinal hypersensitivity, comprising mixing both components and applying an effective amount of a composition, e.g., any of Composition 4, et seq. to the teeth, and optionally then rinsing with water or aqueous solution sufficient to enhance precipitation of zinc oxide in complex with cysteine from the composition.

Also provided is a method of making a an oral care product, e.g., a dentifrice or mouthrinse, comprising (i) a first component comprising a tetrabasic zinc-amino acid halide and (ii) a second component physically separate from the first component comprising cysteine in free or cosmetically acceptable salt form, e.g., any of Composition 4, et seq. comprising combining an orally acceptable carrier, and optionally glycerol, with zinc amino acid halide in the first component, and/or with cysteine in the second component.

For example, in various embodiments, provided are methods to (i) reduce hypersensitivity of the teeth, (ii) to reduce plaque accumulation, (iii) reduce or inhibit demineralization and promote remineralization of the teeth, (iv) inhibit microbial biofilm formation in the oral cavity, (v) reduce or inhibit gingivitis, (vi) promote healing of sores or cuts in the mouth, (vii) reduce levels of acid producing bacteria, (viii) to increase relative levels of non-cariogenic and/or non-plaque forming bacteria, (ix) reduce or inhibit formation of dental caries, (x), reduce, repair or inhibit pre-carious lesions of the enamel, e.g., as detected by quantitative light-induced fluorescence (QLF) or electrical caries measurement (ECM), (xi) treat, relieve or reduce dry mouth, (xii) clean the teeth and oral cavity, (xiii) reduce erosion, (xiv) whiten teeth; (xv) reduce tartar build-up, and/or (xvi) promote systemic health, including cardiovascular health, e.g., by reducing potential for systemic infection via the oral tissues, comprising mixing both components and applying any of Compositions 4, et seq. as described above to the oral cavity of a person in need thereof, e.g., one or more times per day. Also provided are Compositions 4, et seq. for use in any of these methods.

Also provided is the use of (i) a TBZH-AA or TBZH-TAG complex, and (ii) cysteine in free or orally acceptable salt form in the manufacture of an oral care composition, e.g., in accordance with any of Compositions 4, et seq.

Also provided is the use of (i) a TBZH-AA or TBZH-TAG complex, and (ii) cysteine in free or orally acceptable salt form, to reduce and inhibit acid erosion of the enamel, clean the teeth, reduce bacterially-generated biofilm and plaque, reduce gingivitis, inhibit tooth decay and formation of cavities, and/or reduce dentinal hypersensitivity.

In one embodiment, the TBZH-AA or TBZH-TAG complex is prepared at room temperature by mixing the precursors in an aqueous solution. The in situ formation provides ease of formulation. The precursors can be used instead of first having to form the salt. In another embodiment, the water permitting formation of the salt from the precursor comes from water (e.g., rinsing water, saliva or sweat, depending on the application) that comes into contact with the composition in the course of use.

In some embodiments, the total amount of zinc in the composition is 0.05 to 8% by weight of the total composition. In other embodiments, the total amount of zinc is at least 0.1, at least 0.2, at least 0.3, at least 0.4, at least 0.5, or at least 1 up to 8% by weight of the total composition. In other embodiments, the total amount of zinc in the composition is less than 5, less than 4, less than 3, less than 2, or less than 1 to 0.05% by weight of the total composition. For example, the zinc content may be 2-3%.

In certain embodiments, the TBZH-AA or TBZH-TAG complex is anhydrous for dentifrice compositions that contain less than 10% water by weight. By anhydrous, there is less than 5% by weight water, optionally less than 4, less than 3, less than 2, less than 1, less than 0.5, less than 0.1 down to 0% by weight water. When provided in an anhydrous form, precursors of tetrabasic zinc amino acid halide complex, e.g., TBZC and lysine hydrochloride, will not significantly react. When contacted with a sufficient amount of water, the precursors will then react to form the desired salt which upon further dilution with use forms the desired precipitate on the skin or teeth.

Amino Acids:

The amino acid in the TBZH-AA complex can a basic amino acid. By "basic amino acid" is meant the naturally occurring basic amino acids, such as arginine, lysine, and histidine, as well as any basic amino acid having a carboxyl group and an amino group in the molecule, which is water-soluble and provides an aqueous solution with a pH of 7 or greater. Accordingly, basic amino acids include, but are not limited to, arginine, lysine, citrulline, ornithine, creatine, histidine, diaminobutanoic acid, diaminoproprionic acid, salts thereof or combinations thereof. In a particular embodiment, the basic amino acid is lysine. The basic amino acids for use in making zinc amino acid halide complex are generally provided in the form of the halide acid addition salt, e.g., a hydrochloride. The compositions also comprise cysteine in free or orally or cosmetically acceptable salt form. By "orally or cosmetically acceptable salt form" is meant a salt form which is safe for administration to the oral cavity or skin respectively in the concentrations provided, and which does not interfere with the biological activity of the zinc. In a particular embodiment, the cysteine is administered in free form. Wherever weights are given for amounts of amino acids in formulations herein, the weights are generally provided in terms of the weight of the free acid unless otherwise noted.

In general, the optional ingredients described herein can be present in the first component, the second component or both.

Glycerol

Glycerol or glycerin is an optional ingredient in the first and/or second component of the composition. It has found that the presence of glycerol can delay the precipitation of the TBZH-AA complex when the two components are mixed. Glycerol can also act as a humectant.

Cysteine

The compositions also comprise cysteine in free or orally or cosmetically acceptable salt form. By "orally or cosmetically acceptable salt form" is meant a salt form which is safe for administration to the oral cavity or skin respectively in the concentrations provided, and which does not interfere with the biological activity of the zinc. In a particular embodiment, the cysteine is administered in free form. Wherever weights are given for amounts of amino acids in formulations herein, the weights are generally provided in terms of the weight of the free acid unless otherwise noted. In certain embodiments, the cysteine is a cysteine hydrohalide, such as cysteine hydrochloride.

In compositions comprising an orally or cosmetically acceptable carrier, the carrier represents all other materials in the composition other than TBZH-AA or TBZH-TAG complex (including precursors) and the cysteine. The amount of carrier is thus the amount to reach 100% by adding to the weight of TBZH-AA or TBZH-TAG complex (including precursors) and the protein. By "orally acceptable carrier" is meant a carrier which is suitable for use in an oral care product, consisting of ingredients which are generally recognized as safe for use in amounts and concentrations as provided in a dentifrice or mouthrinse, for example. By "cosmetically acceptable carrier" is meant a carrier which is suitable for use in a product for topical use on the skin, consisting of ingredients which are generally recognized as safe for use in amounts and concentrations as provided in a liquid hand soap or body wash, or in an antiperspirant product, for example. Excipients for use in the compositions thus may include for example excipients which are "Generally Recognized as Safe" (GRAS) by the United States Food and Drug Administration.

Personal Care Formulations:

The term "cosmetically acceptable carrier" thus refers to any formulation or carrier medium that provides the appropriate delivery of an effective amount of the complex as defined herein, does not interfere with the effectiveness of the biological activity of the zinc, and is suitable and nontoxic for topical administration to the skin. Representative carriers include water, oils, both vegetable and mineral, soap bases, cream bases, lotion bases, ointment bases and the like, particularly aqueous detergent carriers, for example liquid hand soaps or body washes. In one embodiment, the aqueous soap bases are free of or contain less than one percent of anionic surfactants. In another embodiment, the cosmetically acceptable carrier contains topically acceptable quaternary ammonium compounds. They may additionally include buffers, preservatives, antioxidants, fragrances, emulsifiers, dyes and excipients known or used in the field of drug formulation and that do not unduly interfere with the effectiveness of the biological activity of the active agent, and that is sufficiently non-toxic to the host or patient. Additives for topical formulations are well-known in the art, and may be added to the topical composition, as long as they are pharmaceutically acceptable and not deleterious to the epithelial cells or their function. Further, they should not cause deterioration in the stability of the composition. For example, inert fillers, anti-irritants, tackifiers, excipients, fragrances, opacifiers, antioxidants, gelling agents, stabilizers, surfactant, emollients, coloring agents, preservatives, buffering agents, and other conventional components of topical formulations as are known in the art.

In some cases, the personal care compositions comprise oils or moisturizers, which may not be water soluble and may be delivered in an emulsion system, wherein the zinc-lysine complex would be in the water phase of the emulsion. Surfactants for the emulsion formulations may comprise a combination of nonionic surfactants, for example, one or more surfactants selected from the group consisting of: (i) lipophilic surfactants, e.g., having an HLB value of 8 or lower, for example sorbitan-fatty acid esters, such as sorbitan oleates, for example, sorbitan sesquioleate; and (ii) hydrophilic surfactants, e.g., having an HLB of greater than 8, particularly a. di- or tri-alkanol amines, such as triethanol amine; b. polyethoxylated surfactants, for example polyethoxylated alcohols (esp. polyethoxylated polyols), polyethoxylated vegetable oils, and polyethoxylated silicones, e.g., polysorbate 80, dimethicone polyethylene oxide, and dimethylmethyl (polyethylene oxide) siloxane. For a water-in-oil emulsion, the overall HLB of the surfactant mixture is preferably 2-8, i.e., there is typically a higher proportion of lipophilic surfactant; whereas for an oil-in-water emulsion, the overall HLB of the surfactant mixture is preferably 8-16.

The personal care compositions may also comprise suitable antioxidants, substances known to inhibit oxidation. Antioxidants suitable for use in the compositions include, but are not limited to, butylated hydroxytoluene, ascorbic acid, sodium ascorbate, calcium ascorbate, ascorbic palmitate, butylated hydroxyanisole, 2,4,5-trihydroxybutyrophenone, 4-hydroxymethyl-2,6-di-fert-butylphenol, erythorbic acid, gum guaiac, propyl gallate, thiodipropionic acid, dilauryl thiodipropionate, tert-butylhydroquinone and tocopherols such as vitamin E, and the like, including pharmaceutically acceptable salts and esters of these compounds. Preferably, the antioxidant is butylated hydroxytoluene, butylated hydroxyanisole, propyl gallate, ascorbic acid, pharmaceutically acceptable salts or esters thereof, or mixtures thereof. Most preferably, the antioxidant is butylated hydroxytoluene. These materials are available from Ruger Chemical Co, (Irvington, N.J.). When the topical formulations contain at least one antioxidant, the total amount of antioxidant present is from 0.001 to 0.5 wt %, preferably 0.05 to 0.5 wt %, more preferably 0.1%.

The personal care compositions may also comprise suitable preservatives. Preservatives are compounds added to a formulation to act as an antimicrobial agent. Among preservatives known in the art as being effective and acceptable in parenteral formulations are benzalkonium chloride, benzethonium, chlorohexidine, phenol, m-cresol, benzyl alcohol, methylparaben, propylparaben, chlorobutanol, o-cresol, p-cresol, chlorocresol, phenylmercuric nitrate, thimerosal, benzoic acid, and various mixtures thereof. See, e.g., Wallhausser, K.-H., Develop. Biol. Standard, 24:9-28 (1974) (S. Krager, Basel). Preferably, the preservative is selected from methylparaben, propylparaben and mixtures thereof. These materials are available from Inolex Chemical Co (Philadelphia, Pa.) or Spectrum Chemicals. When the topical formulations contain at least one preservative, the total amount of preservative present is from 0.01 to 0.5 wt %, preferably from 0.1 to 0.5%, more preferably from 0.03 to 0.15. Preferably the preservative is a mixture of methylparaben and proplybarben in a 5/1 ratio. When alcohol is used as a preservative, the amount is usually 15 to 20%.

The personal care compositions may also comprise suitable chelating agents to form complexes with metal cations that do not cross a lipid bilayer. Examples of suitable chelating agents include ethylene diamine tetraacetic acid (EDTA), ethylene glycol-bis(beta-aminoethyl ether)-N,N,N',N'-tetraacetic acid (EGTA) and 8-Amino-2-[(2-amino-5-methylphenoxy)methyl]-6-methoxyquinoline-$N_5$N,N',N'-tetraacetic acid, tetrapotassium salt (QUIN-2). Preferably the chelating agents are EDTA and citric acid. These materials are available from Spectrum Chemicals. When the topical formulations contain at least one chelating agent, the total amount of chelating agent present is from 0.005% to 2.0% by weight, preferably from 0.05% to 0.5 wt %, more preferably 0.1% by weight. Care must be taken that the chelators do not interfere with the zinc complex, for example by binding zinc, but in the formulations tested, low levels of EDTA, for example, have not presented problems.

The personal care compositions may also comprise suitable viscosity increasing agents. These components are diffusible compounds capable of increasing the viscosity of a polymer-containing solution through the interaction of the agent with the polymer. CARBOPOL ULTREZ 10 may be used as a viscosity-increasing agent. These materials are available from Noveon Chemicals, Cleveland, Ohio. When the topical formulations contain at least one viscosity increasing agent, the total amount of viscosity increasing agent present is from 0.25% to 5.0% by weight, preferably from 0.25% to 1.0 wt %, and more preferably from 0.4% to 0.6% by weight.

Liquid forms, such as lotions suitable for topical administration or suitable for cosmetic application, may include a suitable aqueous or nonaqueous vehicle with buffers, suspending and dispensing agents, thickeners, penetration enhancers, and the like. Solid forms such as creams or pastes or the like may include, for example, any of the following ingredients, water, oil, alcohol or grease as a substrate with surfactant, polymers such as polyethylene glycol, thickeners, solids and the like. Liquid or solid formulations may include enhanced delivery technologies such as liposomes, microsomes, microsponges and the like.

Topical treatment regimens can comprise applying the composition directly to the skin at the application site, from one to several times daily, and washing with water to trigger precipitation of the zinc oxide on the skin.

Formulations can be used to treat, ameliorate or prevent conditions or symptoms associated with bacterial infections, acne, inflammation and the like.

Oral Care Formulations:

The oral care compositions, e.g., Composition 4, et seq. may comprise various agents which are active to protect and enhance the strength and integrity of the enamel and tooth structure and/or to reduce bacteria and associated tooth decay and/or gum disease, including or in addition to the zinc-amino acid-halide complexes. Effective concentration of the active ingredients used herein will depend on the particular agent and the delivery system used. It is understood that a toothpaste for example will typically be diluted with water upon use, while a mouthrinse typically will not be. Thus, an effective concentration of active in a toothpaste will ordinarily be 5-15× higher than required for a mouthrinse. The concentration will also depend on the exact salt or polymer selected. For example, where the active agent is provided in salt form, the counterion will affect the weight of the salt, so that if the counterion is heavier, more salt by weight will be required to provide the same concentration of active ion in the final product. Arginine, where present, may be present at levels from, e.g., 0.1 to 20 wt % (expressed as weight of free base), e.g., 1 to 10 wt % for a consumer toothpaste or 7 to 20 wt % for a professional or prescription treatment product. Fluoride where present may be present at levels of, e.g., 25 to 25,000 ppm, for example 750 to 2,000 ppm for a consumer toothpaste, or 2,000 to 25,000 ppm for a professional or prescription treatment product. Levels of antibacterial agents will vary similarly, with levels used in toothpaste being e.g., 5 to 15 times greater than used in mouthrinse. For example, a triclosan toothpaste may contain 0.3 wt % triclosan.

The oral care compositions may further include one or more fluoride ion sources, e.g., soluble fluoride salts. A wide variety of fluoride ion-yielding materials can be employed as sources of soluble fluoride in the present compositions. Examples of suitable fluoride ion-yielding materials are found in U.S. Pat. No. 3,535,421, to Briner et al.; U.S. Pat. No. 4,885,155, to Parran, Jr. et al. and U.S. Pat. No. 3,678,154, to Widder et al. Representative fluoride ion sources include, but are not limited to, stannous fluoride, sodium fluoride, potassium fluoride, sodium monofluorophosphate, sodium fluorosilicate, ammonium fluorosilicate, amine fluoride, ammonium fluoride, and combinations thereof. In certain embodiments the fluoride ion source includes stannous fluoride, sodium fluoride, sodium monofluorophosphate as well as mixtures thereof. In certain embodiments, the oral care composition may also contain a source of fluoride ions or fluorine-providing ingredient in amounts sufficient to supply 25 ppm to 25,000 ppm of fluoride ions, generally at least 500 ppm, e.g., 500 to 2000 ppm, e.g., 1000 to 1600 ppm, e.g., 1450 ppm. The appropriate level of fluoride will depend on the particular application. A toothpaste for general consumer use would typically have 1000 to 1500 ppm, with pediatric toothpaste having somewhat less. A dentifrice or coating for professional application could have as much as 5,000 or even 25,000 ppm fluoride. Fluoride ion sources may be added to the compositions at a level of 0.01 wt. % to 10 wt. % in one embodiment or 0.03 wt. % to 5 wt. %, and in another embodiment 0.1 wt. % to 1 wt. % by weight of the composition in another embodiment. Weights of fluoride salts to provide the appropriate level of fluoride ion will obviously vary based on the weight of the counterion in the salt.

Abrasives:

The oral care compositions, e.g. Composition 4 et seq. may include silica abrasives, and may comprise additional abrasives, e.g., a calcium phosphate abrasive, e.g., tricalcium phosphate ($Ca_3(PO_4)_2$), hydroxyapatite ($Ca_{10}(PO_4)_6(OH)_2$), or dicalcium phosphate dihydrate ($CaHPO_4*2H_2O$, also sometimes referred to herein as DiCal) or calcium pyrophosphate; calcium carbonate abrasive; or abrasives such as sodium metaphosphate, potassium metaphosphate, aluminum silicate, calcined alumina, bentonite or other siliceous materials, or combinations thereof.

Other silica abrasive polishing materials useful herein, as well as the other abrasives, generally have an average particle size ranging between 0.1 and 30 microns, between 5 and 15 microns. The silica abrasives can be from precipitated silica or silica gels, such as the silica xerogels described in U.S. Pat. No. 3,538,230, to Pader et al. and U.S. Pat. No. 3,862,307, to Digiulio. Particular silica xerogels are marketed under the trade name Syloid® by the W. R. Grace & Co., Davison Chemical Division. The precipitated silica materials include those marketed by the J. M. Huber Corp. under the trade name Zeodent®, including the silica carrying the designation Zeodent 115 and 119. These silica abrasives are described in U.S. Pat. No. 4,340,583, to Wason. In certain embodiments, abrasive materials useful in the practice of the oral care compositions include silica gels and precipitated amorphous silica having an oil absorption value of less than 100 cc/100 g silica and in the range of 45 cc/100 g to 70 cc/100 g silica. Oil absorption values are measured using the ASTA Rub-Out Method D281. In certain embodiments, the silicas are colloidal particles having an average particle size of 3 microns to 12 microns, and 5 to 10 microns. Low oil absorption silica abrasives particularly useful in the compositions are marketed under the trade designation Sylodent XWA® by Davison Chemical Division of W.R. Grace & Co., Baltimore, Md. 21203. Sylodent 650 XWA®, a silica hydrogel composed of particles of colloidal silica having a water content of 29% by weight averaging 7 to 10 microns in diameter, and an oil absorption of less than 70 cc/100 g of silica is an example of a low oil absorption silica abrasive useful in the composition.

Foaming Agents:

The oral care compositions also may include an agent to increase the amount of foam that is produced when the oral cavity is brushed. Illustrative examples of agents that increase the amount of foam include, but are not limited to polyoxyethylene and certain polymers including, but not limited to, alginate polymers. The polyoxyethylene may increase the amount of foam and the thickness of the foam generated by the oral care carrier component of the composition. Polyoxyethylene is also commonly known as polyethylene glycol ("PEG") or polyethylene oxide. The polyoxyethylenes suitable for this composition will have a molecular weight of 200,000 to 7,000,000. In one embodiment the molecular weight will be 600,000 to 2,000,000 and in another embodiment 800,000 to 1,000,000. Polyox® is the trade name for the high molecular weight polyoxyethylene produced by Union Carbide. The polyoxyethylene may be present in an amount of 1% to 90%, in one embodiment 5% to 50% and in another embodiment 10% to 20% by weight of the oral care carrier component of the oral care compositions. Where present, the amount of foaming agent in the oral care composition (i.e., a single dose) is 0.01 to 0.9% by weight, 0.05 to 0.5% by weight, and in another embodiment 0.1 to 0.2% by weight.

Surfactants:

The compositions may contain anionic, cationic, nonionic and/or zwitterionic surfactants, for example:
i. water-soluble salts of higher fatty acid monoglyceride monosulfates, such as the sodium salt of the monosulfated monoglyceride of hydrogenated coconut oil fatty acids such as sodium N-methyl N-cocoyl taurate, sodium cocomonoglyceride sulfate.
ii. higher alkyl sulfates, such as sodium lauryl sulfate,
iii. higher alkyl-ether sulfates, e.g., of formula $CH_3(CH_2)_m CH_2(OCH_2CH_2)_n OSO_3X$, wherein m is 6-16, e.g., 10, n is 1-6, e.g., 2, 3 or 4, and X is Na or K, for example sodium laureth-2 sulfate $(CH_3(CH_2)_{10}CH_2(OCH_2CH_2)_2 OSO_3Na)$.
iv. higher alkyl aryl sulfonates such as sodium dodecyl benzene sulfonate (sodium lauryl benzene sulfonate)
v. higher alkyl sulfoacetates, such as sodium lauryl sulfoacetate (dodecyl sodium sulfoacetate), higher fatty acid esters of 1,2 dihydroxy propane sulfonate, sulfocolaurate (N-2-ethyl laurate potassium sulfoacetamide) and sodium lauryl sarcosinate.

By "higher alkyl" is meant, e.g., $C_{6-30}$ alkyl. In particular embodiments, the anionic surfactant is selected from sodium lauryl sulfate and sodium ether lauryl sulfate. The anionic surfactant may be present in an amount which is effective, e.g., >0.01% by weight of the formulation, but not at a concentration which would be irritating to the oral tissue, e.g., <10%, and optimal concentrations depend on the particular formulation and the particular surfactant. For example, concentrations used or a mouthwash are typically on the order of one tenth that used for a toothpaste. In one embodiment, the anionic surfactant is present in a toothpaste at 0.3% to 4.5% by weight, e.g., 1.5%. The compositions may optionally contain mixtures of surfactants, e.g., comprising anionic surfactants and other surfactants that may be anionic, cationic, zwitterionic or nonionic. Generally, surfactants are those which are reasonably stable throughout a wide pH range. Surfactants are described more fully, for example, in U.S. Pat. No. 3,959,458, to Agricola et al.; U.S. Pat. No. 3,937,807, to Haefele; and U.S. Pat. No. 4,051,234, to Gieske et al. In certain embodiments, the anionic surfactants useful herein include the water-soluble salts of alkyl sulfates having 10 to 18 carbon atoms in the alkyl radical and the water-soluble salts of sulfonated monoglycerides of fatty acids having 10 to 18 carbon atoms. Sodium lauryl sulfate, sodium lauroyl sarcosinate and sodium coconut monoglyceride sulfonates are examples of anionic surfactants of this type. In a particular embodiment, the composition, e.g., Composition 4, et seq., comprises sodium lauryl sulfate.

The surfactant or mixtures of compatible surfactants can be present in the composition in 0.1% to 5%, in another embodiment 0.3% to 3% and in another embodiment 0.5% to 2% by weight of the total composition.

Note that care must be taken that the anionic surfactants do not interfere with zinc amino acid halide complex or with the activity of the zinc. At relatively low levels and in a relatively low water formulation, the surfactants generally would not have major impact, but higher levels of anionic surfactant, particularly in aqueous formulations, anionic surfactants can be excluded. Cationic and/or nonionic surfactants may be utilized instead.

Tartar Control Agents:

In various embodiments, the compositions comprise an anticalculus (tartar control) agent. Suitable anticalculus agents include without limitation phosphates and polyphosphates (for example pyrophosphates), polyaminopropanesulfonic acid (AMPS), hexametaphosphate salts, zinc citrate trihydrate, polypeptides, polyolefin sulfonates, polyolefin phosphates, diphosphonates. The composition thus may comprise phosphate salts. In particular embodiments, these salts are alkali phosphate salts, i.e., salts of alkali metal hydroxides or alkaline earth hydroxides, for example, sodium, potassium or calcium salts. "Phosphate" as used herein encompasses orally acceptable mono- and polyphosphates, for example, $P_{1-6}$ phosphates, for example monomeric phosphates such as monobasic, dibasic or tribasic phosphate; dimeric phosphates such as pyrophosphates; and multimeric phosphates, e.g., sodium hexametaphosphate. In particular examples, the selected phosphate is selected from alkali dibasic phosphate and alkali pyrophosphate salts, e.g., selected from sodium phosphate dibasic, potassium phosphate dibasic, dicalcium phosphate dihydrate, calcium pyrophosphate, tetrasodium pyrophosphate, tetrapotassium pyrophosphate, sodium tripolyphosphate, and mixtures of any of two or more of these. In a particular embodiment, for example the compositions comprise a mixture of tetrasodium pyrophosphate ($Na_4P_2O_7$), calcium pyrophosphate ($Ca_2P_2O_7$), and sodium phosphate dibasic ($Na_2HPO_4$), e.g., in amounts of ca. 3-4% of the sodium phosphate dibasic and ca. 0.2-1% of each of the pyrophosphates. In another embodiment, the compositions comprise a mixture of tetrasodium pyrophosphate (TSPP) and sodium tripolyphosphate (STPP) ($Na_5P_3O_{10}$), e.g., in proportions of TSPP at 1-2% and STPP at 7% to 10%. Such phosphates are provided in an amount effective to reduce erosion of the enamel, to aid in cleaning the teeth, and/or to reduce tartar buildup on the teeth, for example in an amount of 2-20%, e.g., ca. 5-15%, by weight of the composition.

Flavoring Agents:

The oral care compositions may also include a flavoring agent. Flavoring agents which can be used in the composition include, but are not limited to, essential oils as well as various flavoring aldehydes, esters, alcohols, and similar materials. Examples of the essential oils include oils of spearmint, peppermint, wintergreen, sassafras, clove, sage, eucalyptus, marjoram, cinnamon, lemon, lime, grapefruit, and orange. Also useful are such chemicals as menthol, carvone, and anethole. Certain embodiments employ the oils of peppermint and spearmint. The flavoring agent may be incorporated in the oral composition at a concentration of 0.1 to 5% by weight e.g. 0.5 to 1.5% by weight.

Polymers:

The oral care compositions may also include additional polymers to adjust the viscosity of the formulation or enhance the solubility of other ingredients. Such additional polymers include polyethylene glycols, polysaccharides (e.g., cellulose derivatives, for example carboxymethyl cellulose, or polysaccharide gums, for example xanthan gum or carrageenan gum). Acidic polymers, for example polyacrylate gels, may be provided in the form of their free acids or partially or fully neutralized water soluble alkali metal (e.g., potassium and sodium) or ammonium salts.

Silica thickeners, which form polymeric structures or gels in aqueous media, may be present. Note that these silica thickeners are physically and functionally distinct from the particulate silica abrasives also present in the compositions, as the silica thickeners are very finely divided and provide little or no abrasive action. Other thickening agents are carboxyvinyl polymers, carrageenan, hydroxyethyl cellulose and water soluble salts of cellulose ethers such as sodium carboxymethyl cellulose and sodium carboxymethyl hydroxyethyl cellulose. Natural gums such as karaya, gum arabic, and gum tragacanth can also be incorporated. Colloidal magnesium aluminum silicate can also be used as component of the thickening composition to further improve the composition's texture. In certain embodiments, thickening agents in an amount of 0.5% to 5.0% by weight of the total composition are used.

The compositions may include an anionic polymer, for example in an amount of from 0.05 to 5%. Such agents are known generally for use in dentifrice, although not for this particular application, useful in composition are disclosed in U.S. Pat. Nos. 5,188,821 and 5,192,531; and include synthetic anionic polymeric polycarboxylates, such as 1:4 to 4:1 copolymers of maleic anhydride or acid with another polymerizable ethylenically unsaturated monomer, preferably methyl vinyl ether/maleic anhydride having a molecular weight (M.W.) of 30,000 to 1,000,000, most preferably 300,000 to 800,000. These copolymers are available for example as Gantrez. e.g., AN 139 (M.W. 500,000), AN 119 (M.W. 250,000) and preferably S-97 Pharmaceutical Grade (M.W. 700,000) available from ISP Technologies, Inc., Bound Brook, N.J. 08805. The enhancing agents when present are present in amounts ranging from 0.05 to 3% by weight. Other operative polymers include those such as the 1:1 copolymers of maleic anhydride with ethyl acrylate, hydroxyethyl methacrylate, N-vinyl-2-pyrollidone, or ethylene, the latter being available for example as Monsanto EMA No. 1103, M.W. 10,000 and EMA Grade 61, and 1:1 copolymers of acrylic acid with methyl or hydroxyethyl methacrylate, methyl or ethyl acrylate, isobutyl vinyl ether or N-vinyl-2-pyrrolidone. Suitable generally, are polymerized olefinically or ethylenically unsaturated carboxylic acids containing an activated carbon-to-carbon olefinic double bond and at least one carboxyl group, that is, an acid containing an olefinic double bond which readily functions in polymerization because of its presence in the monomer molecule either in the alpha-beta position with respect to a carboxyl group or as part of a terminal methylene grouping. Illustrative of such acids are acrylic, methacrylic, ethacrylic, alpha-chloroacrylic, crotonic, beta-acryloxy propionic, sorbic, alpha-chlorsorbic, cinnamic, beta-styrylacrylic, muconic, itaconic, citraconic, mesaconic, glutaconic, aconitic, alpha-phenylacrylic, 2-benzyl acrylic, 2-cyclohexylacrylic, angelic, umbellic, fumaric, maleic acids and anhydrides. Other different olefinic monomers copolymerizable with such carboxylic monomers include vinylacetate, vinyl chloride, dimethyl maleate and the like. Copolymers contain sufficient carboxylic salt groups for water-solubility. A further class of polymeric agents includes a composition containing homopolymers of substituted acrylamides and/or homopolymers of unsaturated sulfonic acids and salts thereof, in particular where polymers are based on unsaturated sulfonic acids selected from acrylamidoalykane sulfonic acids such as 2-acrylamide 2 methylpropane sulfonic acid having a molecular weight of 1,000 to 2,000,000, described in U.S. Pat. No. 4,842,847, Jun. 27, 1989 to Zahid. Another useful class of polymeric agents includes polyamino acids containing proportions of anionic surface-active amino acids such as aspartic acid, glutamic acid and phosphoserine, e.g. as disclosed in U.S. Pat. No. 4,866,161 Sikes et al.

Water:

The oral compositions may comprise significant levels of water. Water employed in the preparation of commercial oral compositions should be deionized and free of organic impurities. The amount of water in the compositions includes the free water which is added plus that amount which is introduced with other materials.

Humectants:

Within certain embodiments of the oral compositions, it is also desirable to incorporate a humectant to prevent the composition from hardening upon exposure to air. Certain humectants can also impart desirable sweetness or flavor to dentifrice compositions. Suitable humectants include edible polyhydric alcohols such as glycerine, sorbitol, xylitol, propylene glycol as well as other polyols and mixtures of these humectants. In one embodiment, the principal humectant is glycerin, which may be present at levels of greater than 25%, e.g. 25-35% 30%, with 5% or less of other humectants.

Other Optional Ingredients:

In addition to the above-described components, the oral care embodiments can contain a variety of optional dentifrice ingredients some of which are described below. Optional ingredients include, for example, but are not limited to, adhesives, sudsing agents, flavoring agents, sweetening agents, additional antiplaque agents, abrasives, and coloring agents. These and other optional components are further described in U.S. Pat. No. 5,004,597, to Majeti; U.S. Pat. No. 3,959,458 to Agricola et al. and U.S. Pat. No. 3,937,807, to Haefele, all being incorporated herein by reference.

Optional Forms

The form of the dual component system can take the form of a dual chamber form or any other means to separate the components which include, but is not limited to beads, capsules, and films.

Unless stated otherwise, all percentages of composition components given in this specification are by weight based on a total composition or formulation weight of 100%. The term "total composition" or just "composition" means the total final product form, i.e., the combination of the first and second components.

The compositions and formulations as provided herein are described and claimed with reference to their ingredients, as is usual in the art. As would be evident to one skilled in the art, the ingredients may in some instances react with one another, so that the true composition of the final formulation may not correspond exactly to the ingredients listed. Thus, it should be understood that the composition extends to the product of the combination of the listed ingredients.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

Embodiments of the present invention are further described in the following examples. The examples are merely illustrative and do not in any way limit the scope of the invention as described and claimed.

EXAMPLES

A two-stock solution was developed and tested. The two stock system consisted of:

Stock 1: 4.375 mL water+1M HCl+0.005 g Cysteine (HCl amount varying each experiment)

Stock 2: 0.1250 mL TBZC-Lysine Stock

TBZC-Lysine Stock—14.6190 g (0.1 mole) of L-Lysine is dissolved in 100 ml of Deionized water at room temperature under stirring. After all L-Lysine dissolves, 5.5740 g (0.0101 mole) of TBZC is slowly added into the solution under stirring. The suspension is continued mixing at room temperature for at least 30 minutes to 24 hours. Then, the suspension solution is centrifuged at 7000 rpm for 20 minutes and filtered through filter membrane with 0.45 um pore size to remove unreacted TBZC. The yellow clear supernatant is recovered as stock solution.

The final product formed a 36 fold dilution of TBZC-Lysine with water and acid. It also produced a 0.1% solution of cysteine. By varying the amount of acid added, different results were achieved as follows:

Example 1

10 µL 1M HCl in stock 1
pH stock 1: 3.096
pH stock 2: 10.024
pH final: 8.249
reaction delay: no observable reaction
The utilization of 10 µL of HCl was not enough to produce a precipitation within the final solution.

Example 2

20 µL 1M HCl in stock 1
pH stock 1: 2.906
pH stock 2: 10.024
pH final: 7.376
reaction delay: no observable reaction
The utilization of 20 µL of HCl was not enough to produce a precipitation within the final solution.

Example 3

30 µL 1M HCl in stock 1
pH stock 1: 2.681
pH stock 2: 10.024
pH final: 7.141
reaction delay: 3 seconds
By lowering the pH to 7.141 the solution effectively produced a precipitation after about 3 seconds of mixing.

Example 4

40 µL HCl in stock 1
pH stock 1: 2.441
pH stock 2: 10.024
pH final: 6.430
reaction delay: 3 seconds
By further lowering the pH of the solution, precipitation was still achieved after about 3 seconds of mixing.

In an additional example, it can be seen that utilizing cysteine HCl can have a similar effect in comparison to acidified aqueous cysteine.

Example 5

Stock 1: 4.375 mL deionized water+0.0225 g cysteine HCl
Stock 2: 0.1250 mL TBZC-lysine
pH of stock 1: 2.104
pH of stock 2: 10.456
pH of final product: 5.002
observable precipitation: present instantaneously
In the above example, it is seen that 0.5 wt % cysteine HCl can produce a precipitation similar to how acidified aqueous cysteine can. The final result is a lower pH and a differing range of pH values where precipitation is achieved. In order to slow this reaction for consumers, a co-solvent may desirable.

It was found that the highest amount of observable precipitation within the aqueous acidified cysteine and TBZC-lysine solution was achieved around a pH of 6.3. The observable precipitation would remain as a thick "cloudy" state until approximately 6.0 where it then began to dissipate. The solution began to steadily clarify around pH 5.7, and became completely clear by pH 5.3.

Example 6

The reaction delay can be important for oral care applications in particular. By adding glycerin to the second stock (TBZC-Lysine) one can effectively lengthen the reaction delay to a desired amount. For example:

Stock 1: 0.005 g Cysteine+30 µL 1M HCl+4.375 mL deionized water
Stock 2: 8.750 g Glycerin+0.1250 mL TBZC-Lysine
(glycerin is approximately 66% by weight of the final solution)
pH stock 1: 2.681
pH stock 2: indistinguishable
final pH: 6.927
time delay: 10+ Seconds By adding glycerin in an amount that comprises approximately 66 wt % of the final solution, one can increase the reaction delay to over 10 seconds. Note, the pH of stock 2 was indistinguishable due to the pH probe's incompatibility with viscous liquids. Also note that the time delay was approximately 10 seconds of vigorous mixing. In actual applications the delay would most likely be longer due to less-intense mixing methods.

C. Conclusions

In summary, the invention consists of a two stock solution. The first stock contains an aqueous solution of acidified cysteine or cysteine-HCl. The second stock contains TBZC-lysine with a variable amount of glycerin. By utilizing a two stock system, the reaction rate can be altered to allow consumers the full benefit of the product within the oral cavity. Furthermore, the two stock system produces a safer pH that will allow for usage within the oral care field.

Example 7

Liquid Hand Soap with TBZC-Lys and Cysteine 1 g of TBZC-lys of Example 5 (prior to dilution to form the "stock" solution) is combined with 4 g of a commercial liquid hand soap (LHS) having a formulation as set forth in Table 1, to provide a formulation having 0.7% zinc.

TABLE 1

| Material | Weight % |
| --- | --- |
| Cetrimonium chloride (cetyl trimethyl ammonium chloride) | 2.4 |
| Glycerin | 2 |
| Lauramidopropyldimethylamine oxide | 1.2 |
| Cocamide MEA (cocomonoethanolamide) | 1 |
| PEG-120 methyl glucose dioleate | 0.6 |
| Myristamidopropylamine oxide | 0.4 |
| $C_{12-18}$ alkyldimethylbenzyl ammonium chloride (BKC) | 0.13 |
| Water and minors | Q.S. |

In a soap container, the bottle is divided by a barrier. Both sides of the barrier contain the standard soap base in the table immediately above. One side contains the appropriate amount of cysteine and the other side contains the appropriate amount of TBZC-lys. When dispensed, the two stocks will mix in the nozzle forming an instantaneous precipitation directly to the skin's surface without having a reaction occur within the bottle that may expend all the desired benefits.

Example 8

Gel Formulations Comprising Zinc-Lysine

An oral gel toothpaste with TBZC-lys/cysteine as active ingredient is formulated with the ingredients shown in Table 2.

TABLE 2

| Oral gel with ZLC/cysteine | | |
| --- | --- | --- |
| Ingredients | % | Loading (g) |
| Sorbitol 70% sol | 76.03% | 380.15 |
| Aqueous TBZC-lys solution 2.53% Zn | 10.00% | 50 |
| Cysteine 0.5% | 10.00% | 50 |
| Carboxymethyl cellulose (CMC) and Trimethyl cellulose (TMC) | 0.70% | 3.5 |
| Na Saccharin | 0.27% | 1.35 |
| Propylene Glycol | 3.00% | 15 |
| Total | 100.00% | 500 |
| % Zn | 0.506% | |
| Propylene Glycol | 3.00% | 15 |
| DI water | 15.07% | 75.35 |
| Total | 100.00% | 500 |

The ingredients are placed in a tube. The tube is separated by means of either a physical divider resulting in two chambers, one chamber containing cysteine and the other containing TBZC-lys. When dispensed, the formulation does not react due to the appropriate desired delay. Upon mixing and brushing a precipitate forms to occlude tubules and provides zinc ion benefits to the oral surfaces.

The invention claimed is:

1. A dual component composition to deliver zinc to a body which comprises (i) a first component comprising a tetrabasic zinc-amino acid-halide complex or a tetrabasic zinc-trialkyl glycine-halide complex and (ii) a second component comprising cysteine in free or in orally or cosmetically acceptable salt form, the first and second components being maintained separate from each other until dispensed and combined for application to the body; and wherein upon mixing the two components, a precipitate is provided comprising zinc oxide in complex with cysteine.

2. The dual component composition of claim 1 further comprising glycerol in the first component, in the second component or in both components.

3. The dual component composition according to claim 1 wherein the pH of the first component is 7 to 11, 8 to 10 or 9 to 10, and the pH of the second component is 2 to 6, 2 to 5, 3 to 6 or 4.5 to 5.5.

4. The composition according to claim 1, wherein the tetrabasic zinc-amino acid-halide complex or tetrabasic zinc-trialkyl glycine-halide complex is formed from precursors, wherein the precursors are a zinc ion source, an amino acid source, and a halide source, wherein the halide source can be part of the zinc ion source, the amino acid source, or a halogen acid.

5. The composition according to claim 4, wherein the zinc ion source is tetrabasic zinc chloride.

6. The composition according to claim 4, wherein the amino acid source is at least one of a basic amino acid, lysine, arginine, and glycine.

7. The composition according to claim 1, wherein the trialkyl glycine is a $C_1$-$C_4$ alkyl glycine or trimethyl glycine.

8. The composition according to claim 1 wherein the tetrabasic zinc-amino acid halide complex is made by combining tetrabasic zinc with an amino acid hydrohalide.

9. The composition according to claim 1, which upon mixing the two components, has a pH of 4 to 8, 5 to 8, or 5 to 7, and forms a precipitate in 1 to 20 seconds after mixing.

10. The composition according to claim 1 wherein the total amount of zinc present in the composition is 0.2 to 8% by weight of the total composition.

11. The composition according to claim 1 wherein the amount of cysteine is 0.1% to 1%.

12. The composition according to claim 1, wherein the cysteine is cysteine hydrohalide.

13. The composition according to claim 1, wherein the precipitate is resistant to acid at least a pH of 5.5.

14. The composition according to claim 1 wherein the dual component is selected from the group consisting of dual chamber, beads, capsules, and films.

15. The composition according to claim 1 which is an antiperspirant or deodorant product, further comprising a cosmetically acceptable carrier.

16. A method of killing bacteria, reducing perspiration, and/or reducing body odor comprising mixing the two components of claim 15 and applying to skin an effective amount of the mixed components.

17. The composition of claim 1 which is a personal care product selected from liquid hand soap, body wash, dermal lotions, dermal creams, and dermal conditioners further comprising a cosmetically acceptable carrier in the first component, the second component, or in both components.

18. A method of killing bacteria, treating or reducing the incidence of acne or topical skin infections, or to provide a visual signal when washing, comprising mixing the two components of claim 17 and then washing the skin with water and an effective amount of the mixed components.

19. The composition of claim 1 which is an oral care product, further comprising an orally acceptable carrier in the first component, the second component, or in both components.

20. A method to reduce and inhibit acid erosion of the enamel, clean the teeth, reduce bacterially-generated biofilm and plaque, reduce gingivitis, inhibit tooth decay and formation of cavities, and/or reduce dentinal hypersensitivity comprising mixing the components of claim 19 and applying an effective amount of the mixed components to the oral cavity of a person in need thereof.

21. A method of manufacturing a composition according to claim 1, comprising the step of incorporating a tetrabasic zinc-amino acid-halide complex or tetrabasic zinc-trialkyl glycine-halide complex in one component and cysteine in free or orally acceptable salt form in a second component, during manufacture of the composition.

22. The composition of claim 12, wherein the cysteine hydrohalide is cysteine hydrochloride.

* * * * *